United States Patent [19]

Evenden et al.

[11] Patent Number: 5,962,514
[45] Date of Patent: Oct. 5, 1999

[54] COMBINATION OF 5-HT UPTAKE INHIBITOR WITH A SELECTIVE 5-HT1A ANTAGONIST

[75] Inventors: John Evenden, Stockholm; Seth-Olov Thorberg, Järna, both of Sweden

[73] Assignee: Astra Aktiebolag, Sodertalje, Sweden

[21] Appl. No.: 08/640,896

[22] PCT Filed: Apr. 23, 1996

[86] PCT No.: PCT/SE96/00526

§ 371 Date: May 9, 1996

§ 102(e) Date: May 9, 1996

[87] PCT Pub. No.: WO96/33710

PCT Pub. Date: Oct. 31, 1996

[30] Foreign Application Priority Data

Apr. 27, 1995 [SE] Sweden .................................. 9501567

[51] Int. Cl.⁶ ........................... A61K 31/35; A61K 31/40
[52] U.S. Cl. ........................... 514/456; 514/217; 514/357
[58] Field of Search ..................... 514/217, 456, 514/357

[56] References Cited

U.S. PATENT DOCUMENTS

| 4,698,342 | 10/1987 | Crosby ...................................... 514/253 |
| 5,616,610 | 4/1997 | Evenden et al. .......................... 514/456 |

FOREIGN PATENT DOCUMENTS

WO9511891  5/1995  WIPO .

OTHER PUBLICATIONS

Artigas, et al., *Arch. Gen. Psychiatry* 51, 248–251 (1994).

*Primary Examiner*—Frederick Krass
*Attorney, Agent, or Firm*—White & Case L.L.P.

[57] ABSTRACT

The invention relates to a combination of a first component (a) which is a 5-HT reuptake inhibitor and a second component (b) which is selective 5-HT$_{1A}$ antagonist of the general formula

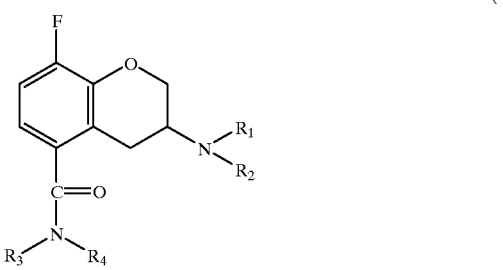

(I)

wherein $R_1$ is n-propyl or cyclobutyl;

$R_2$ is isopropyl, tertiary butyl, cyclobutyl, cyclopentyl or cyclohexyl;

$R_3$ is hydrogen;

$R_4$ is hydrogen or methyl;

as (R)-enantiomer in the form of free base or pharmaceutically acceptable salts thereof, the preparation thereof, pharmaceutical formulations containing said combination, use of and method of treatment of affective disorders such as depression, anxiety and OCD with said combination as well as a kit containing said combination.

27 Claims, 1 Drawing Sheet

Fig. 1

COMBINATION OF 5-HT UPTAKE INHIBITOR WITH A SELECTIVE 5-HT1A ANTAGONIST

This application is a 371 of PCT/SE96/00526 filed Apr. 23, 1996.

FIELD OF THE INVENTION

The present invention relates to a combination of a 5-HT reuptake inhibitor and a selective 5-HT$_{1A}$ antagonist, more specific (R)-5-carbamoyl-8-fluoro-3-N,N-disubstituted-amino-3,4-dihydro-2H-1-benzopyrans in the form of free base or pharmaceutically acceptable salts thereof, process for the preparation of the combination, pharmaceutical formulation containing said combination and to the use of said combination either by coadministration or by individual administration for improvement of the treatment of affective disorders such as depression, anxiety, obsessive compulsive disorder (OCD), etc.

BACKGROUND OF THE INVENTION

Today, it is generally considered that antidepressants, including Selective 5-HT Reuptake Inhibitors (SSRIs), take 2–4 weeks to reach full clinical effect. In contrast, the side effects occur immediately, and even reduce during this period. Thus, slow onset of action of antidepressants lead to a vulnerable period for patients in which they experience the side effects, but not the therapeutic effects of drugs. There is often a heavy burden on the treating physician to persuade the patient to continue with the treatment during this period. Furthermore, in suicidal patients, as the onset of action is gradual, they may regain initiative without experiencing full reversal symptoms, leading a window of risk for suicide and a frequent requirement for hospitalisation. An antidepressant with fast onset of action would not only be benificial due to the faster symptom reduction, but would also be more acceptable to patients and physicians and reduce the need for and duration of hospitalisation. The same long period to reach full clinical effect has been shown in the treatment of other affective disorders such as anxiety and OCD.

PRIOR ART

In Arch. Gen. Psychiatry, vol. 51. Mar.1994 is described that a beta blocker such as pindolol which also has high affinity to 5-HT receptors and antagonize 5-HT$_{1A}$ mediated responses induces a rapid improvement of depressed patients treated with serotonin reuptake inhibitors.

SUMMARY OF THE INVENTION

Antagonism of the acute 5-HT reuptake inhibitor induced decrease in 5-HT turnover by selective 5HT$_{1A}$ antagonists Selective 5-HT reuptake inhibitors (SSRIs) decrease the impulse propagation in 5-HT neurons via a negative feedback reaction probably mediated by collateral 5-HT axons releasing 5-HT in raphé nuclei. By inhibiting the somato-dendritic 5-HT$_{1A}$ autoreceptors the selective antagonists counteract the decrease in 5-HT turnover caused by 5-HT reuptake inhibitors. This indicates that a selective blockade of somatodendritic autoreceptor i.e. 5-HT$_{1A}$ antagonist may have a clinical potential to improve the efficacy of 5-HT reuptake inhibitors (SSRIs) and offer a new rational for rapid onset of affective actions, for instance the antidepressant actions.

The combination

Thus, by combining a first component (a) which is a 5-HT reuptake inhibitor with a second component (b) which is a selective 5-HT$_{1A}$ antagonist of the formula (I)

wherein
  R$_1$ is n-propyl or cyclobutyl;
  R$_2$ is isopropyl, tertiary butyl, cyclobutyl, cyclopentyl or cyclohexyl;
  R$_3$ is hydrogen;
  R$_4$ is hydrogen or methyl;
said 5-HT$_{1A}$-antagonist being in the form of its (R)-enantiomer, and said components (a) and (b) being in the form of free base or pharmaceutically acceptable salts thereof, a faster onset of action will occur and consequently, a more efficacious treatment of the patients.

The following 5-HT$_{1A}$ antagonists may be included as component (b) in the combination of the invention:
  (R)-3-(N-Cyclopentyl-N-n-propylamino)-8-fluoro-5-methylcarbamoyl-3,4-dihydro-2H-1-benzopyran
  (R)-8-Fluoro-3-(N-isopropyl-N-n-propylamino)-5-carbamoyl-3,4-dihydro-2H-1-benzopyran
  (R)-5-Carbamoyl-3-(N-tert-Butyl-N-n-propylamino)-8-fluoro-3,4-dihydro-2H-1-benzopyran
  (R)-5-Carbamoyl-3-(N,N-dicyclobutylamino)8-fluoro-3,4-dihydro-2H-1-benzopyran
  (R)-5-Carbamoyl-3-(N-cyclobutyl-N-propylamino)-8-fluoro-3,4-dihydro-2H-1-benzopyran
  (R)-5-Carbamoyl-3-(N-cyclobutyl-N-isopropylamino)-8-fluoro-3,4-dihydro-2H-1-benzopyran
  (R)-5-Carbamoyl-3-(N-cyclopentyl-N-n-propylamino)-8-fluoro-3,4-dihydro-2H-1-benzopyran
  (R)-5-Carbamoyl-3-(N-cyclohexyl-N-n-propylamino)-8-fluoro-3,4-dihydro-2H-1-benzopyran
  (R)-5-Carbamoyl-3-(N-cyclopentyl-N-cyclobutylamino)-8-fluoro-3,4-dihydro-2H-1-benzopyran The (R)-5-carbamoyl-8-fluoro-3-N,N-disubstituted-amino-3,4-dihydro-2H-1-benzopyrans disclosed herein are described in WO 95/11891 (PCT/SE94/01010).

The (R)-5-carbamoyl-8-fluoro-3-N,N-disubstituted-amino-3,4-dihydro-2H-1-benzopyrans are in the form of free base or pharmaceutically acceptable salt thereof. Both organic and inorganic acids can be employed to form non-toxic pharmaceutically acceptable acid addition salts of the compounds of this invention. Illustrative acids are sulfuric, nitric, phosphoric, oxalic, hydrochloric, formic, hydrobromic, citric, acetic, lactic, tartaric, dibenzoyltartaric, diacetyltartaric, pamoic, ethane-disulfonic, sulfamnic, succinic, propionic, glycollic, malic, gluconic, pyruvic, phenylacetic, 4-aminobenzoic, anthranilic, salicylic, 4-aminosalicylic, 4-hydroxybenzoic, 3,4-dihydroxybenzoic, 3,5-dihydroxybenzoic, 3-hydroxy-2-naphthoic, nicotinic, methanesulfonic, ethanesulfonic, hydroxyethanesulfonic, benzenesulfonic, p-toluenesulfonic, sulfanilic, naphthalenesulfonic, ascorbinic, cyclohexyl-sulfamic, fumaric, maleic and benzoic adds. These salts are readily prepared by methods known in the art.

Those (R)-5-carbamoyl-8-fluoro-3-N,N-disubstituted-amino-3,4-dihydro-2H-1-benzopyrans possess a high affinity to the specific subgroup of $5\text{-HT}_{1A}$ receptor in CNS and act as antagonists on that $5\text{-HT}_{1A}$ receptor, and as well show sufficient bioavailability after oral administration.

Suitable known 5-HT reuptake inhibitors (SSRIs) to be used are norzimeldine, fluoxetine, paroxetine, citalopram, clomipramine, sertraline, fluvoxamine, alaproclate but component (a) in the combination according to the invention is not limited only to those SSRIs.

The combination according to the present invention may be produced in one pharmaceutical formulation comprising both the active first component (a) and the active second component (b) or in two different pharmaceutical formulations, one for the active first component (a) and one for the active second component (b). The pharmaceutical formulation may be in the form of tablets or capsules, powders, mixtures, solutions or other suitable pharmaceutical formulation forms.

The combination of the present invention can be prepared by incorporation of a 5-HT receptable inhibitor into the same preparation as a selective $5\text{-HT}_{1A}$ antagonist as defined above by e.g. mixing in a conventional way.

The present invention also includes a method of improving the onset of therapeutic action by coadministration of a combination of a first component (a) which is a 5-HT reuptake inhibitor and a second component (b) which is a selective $5\text{-HT}_{1A}$ antagonist as herein described.

A further embodiment of the present invention is a kit containing the combination of a first component (a) which is a 5-HT reuptake inhibitor and a second component (b) which is a selective $5\text{-HT}_{1A}$ antagonist, optionally with instructions for use.

DETAILED DESCRIPTION OF THE INVENTION

Methods of preparation of the (R)-5-carbamoyl-8-fluoro-3-N,N-disubstituted-amino-3 4-dihydro-2H-1-benzopyrans The preparation of (R)-3-amino-5-methoxy-3,4dihydro-2H-1-benzopyran (compound II) is described in WO93/07135, the contents of which are hereby incorporated by reference in their entirety. The preferred method for the introduction of fluorine is by brominating the aromatic ring, selectively, in the 8-position. Bromination can be done by using bromine with or without a catalyst. Other brominating agents can be used e.g. HOBr and N-bromo amnides (especially N-bromosucdnimide). Suitable solvents for bro- mination are acetic acid, dioxane and chlorinated solvents e.g. methylene chloride.

Before fluorination the primary amine must be fully alkylated by $R_1$ and by $R_2$ as stated above or protected by a suitable group that can be removed later e.g. dibenzyl. Introduction of the alkyl groups on nitrogen can be done by reductive amination from the appropriate aldehyde or ketone using a suitable reducing agent e.g. $NaCNBH_3$ or catalytically with $H_2$ and a suitable catalyst containing palladium, platinum or nickel in a suitable solvent e.g. tetrahydrofuran (THF), dioxane, methanol or ethanol. Introduction of the alkyl groups can also be done by alkylation with the appropriate alkyl halide e.g. Cl, Br or I, or by an activated alcohol e.g. alkyl-mesylate or -tosylate in a suitable solvent e.g. dimethylformamide (DMF), acetone or acetonitrile with a suitable base e.g. $K_2CO_3$.

Fluorination can then occur by lithiation of the bromo compound with an alkyllithium reagent e.g. n-butyllithium and followed by the reaction with a suitable fluorinating agent preferably a N-fluoro-N-alkyl-/arylsulfonamide e.g. N-fluorobenzenesulfonimide. The solvent for this reaction can be anhydrous alkyl ethers e.g. tetrahydrofuran (THF) or diethyl ether, or non-protic solvents e.g. hexane or benzene. The temperature range can vary from $-100°$ C. to room temperature but preferably $-78°$ C. to $-20°$ C.

The compounds may be prepared from the compound (R)-3-amino-8-fluoro-5-methoxy-3,4-dihydro-2H-1-benzopyran (as described above) followed by known methods such as reductive amination, N-alkylation, demethylation and conversion to the leaving group Y to obtain compound IV.

The compounds of formula I may be prepared according to the following methods:

i, converting directly the compounds of formula IV (IV)

wherein Y is a leaving group such as trifluoromethane sulfonate ($OSO_2CF_3$), halide e.g. Cl, Br or I by a catalytic cycle using a zerovalent transition metal (M) such as Pd or Ni, which may be generated in situ and undergoes an oxidative addition to the aryl-Y-bond. Treatment with carbon monoxide followed by amination with the proper amine (ammonia or methylamine) give the compounds of formula I, whereafter if desired it is converted to a salt.

ii, Alternatively, the compounds of formula IV are converted to the compounds of formula V (V)

wherein Z is Cl, Br, OH or $OR_P$, where $R_P$ is $C_1$–$C_6$ aklayl, by a catalytic cycle using a zerovalent transition metal, with ability to undergo oxidative addition to aryl-Y-bonds e.g. the aryl-$OSO_2CF_3$ bonds. The aryl-CO-metal-Y complex is formed by treatment with carbon monoxide (CO).

Further reagents are an alcohol such as methanol, ethanol, a tertiary amine such as a trialkylamine e.g. triethylamine in an inert organic solvent preferentially a polar aprotic solvent such as dimethylformamide (DMF), dimethylsulfoxide (DMSO), dioxane, tetrahydrofuuran (THF), acetone, acetonitrile etc. The reaction is normally performed at a temperature between +40 to +120° C. and at a pressure between 100 to 500 kPa (ii). This is optionally followed by hydrolysis and treatment with a thionyl halide e.g. thionyl chloride, to obtain the corresponding add halide derivative.

The compounds of formula V is aminated ($ii_b$) with the proper amine (ammonia or methylamine) in a solvent e.g. toluene, methylene chloride, benzene, water at reflux temperature or between 0–100° C. to give the compounds of formula I.

Pharmaceutical formulations

According to the present invention the compounds in the combination will normally be administered orally, rectally or by injection, in the form of pharmaceutical formulations comprising the active ingredient either as a free base or a pharmaceutically acceptable non-toxic acid addition salt, e.g. the hydrochloride, hydrobromide, lactate, acetate, phosphate, sulfate, sulfamate, citrate, tartrate, oxalate and the like in a pharmaceutically acceptable dosage form. The dosage form may be a solid, semisolid or liquid formulation. Usually the active substances will constitute between 0.1 and 99% by weight of the formulation, more specifically between 0.5 and 20% by weight for formulations intended for injection and between 0.2 and 50% by weight for formulations suitable for oral administration.

To produce pharmaceutical formulations of the combination of the invention in the form of dosage units for oral application, the selected compounds may be mixed with a solid excipient, e.g. lactose, saccharose, sorbitol, mannitol, starches such as potato starch, corn starch or amylopectin, cellulose derivatives, a binder such as gelatine or polyvinylpyrrolidone, disintegrants e.g. sodium starch glycolate, cross-linked PVP, cross-caramellose sodium and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablets can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compounds.

For the formulation of soft gelatine capsules, the active substances may be admixed with e.g. a vegetable oil or poly-ethylene glycol. Hard gelatine capsules may contain granules of the active substances using either the above mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substances in a mixture with a neutral fatty base, or gelatine rectal capsules comprising the active substances in admixture with vegetable oil or paraffin oil. Liquid formulations for oral application may be in the form of syrups or suspensions, for example solutions containing from about 0.2% to about 20% by weight of the active substances herein described, the balance being sugar and mixture of ethanol, water, glycerol and propylene glycol. Optionally such liquid formulations may contain colouring agents, flavouring agents, saccharine and carboxymethylcellulose as a thickening agent or other excipients known to a person skilled in the art.

Solutions for parenteral applications by injection can be prepared in an aqueous solution of a water-soluble pharmaceutically acceptable salt of the active substances, preferably in a concentration of from about 0.5% to about 10% by weight. These solutions may also contain stabilizing agents and/or buffering agents and may conveniently be provided in various dosage unit ampoules.

Suitable daily doses of the active compounds in the combination of the invention in therapeutical treatment of humans are about 0.01–100 mg/kg bodyweight at peroral administration and 0.001–100 mg/kg bodyweight at parenteral administration. The daily doses of the active 5-$HT_{1A}$ antagonist may very well differ from the daily doses of the 5-HT reuptake inhibitor, but the doses can also be the same of both the active compounds.

Preparation of Starting Materials for the 5-$HT_{1A}$-antagonists

Preparation 1

(R)-3-Amino-8-fluoro-5methoxy-3,4-dihydro-2H-1-benzopyran a) (R)-3-Amino-8-bromo-5methoxy-3,4-dihydro-2H-1-benzopyran (R)-3-Amino-5-methoxy-3,4dihydro-2H-1-benzopyran (25 g, 0.14 mol; prepared as described in WO93/07135) and anhydrous sodium acetate (34 g, 0.42 mol) were dissolved in acetic acid (500 mL). Bromine (23.4 g, 0.15 mol), dissolved in acetic acid (500 mL), was added dropwise at room temperature. The addition of bromine continued for about 7 days. The solvent was removed in vacuo and the residue was dissolved in sodium hydroxide (25%)/diethyl ether (exothermic reaction, the mixture was cooled in an ice-bath). The layers were separated and the alkaline water-phase was extracted thrice with diethyl ether. The combined ether layers were dried ($Na_2SO_4$) and the solvent was removed in vacuo to give 35.5 g of an oily residue. The oil was dissolved in diethyl ether and the solution was cooled with an ice-bath (0° C.). HCl, dissolved in diethyl ether, was added dropwise until the suspension became acidic (controlled with pH paper). The crystals were filtered and then recrystallized from methanol to give the title compound in 70% yield (28.5 g). Mp: 281–282° C. The HCl salt was partitioned between diethyl ether and 2M $NH_3$ (aq) and the free base was obtained by extractions of the alkaline water phase with diethyl ether. $[\alpha]^{21}_D$=+40° (C=0.1, HCl salt in MeOH). GC-MS (70 eV) M+1=259 (53%).

b) (R)-8-Bromo-3-(N,N-dibenzylamino)-5-methoxy-3,dihydro-2H-1-benzopyran (R)-3-Amino-8-bromo-5-methoxy-3,4-dihydro-2H-1-benzopyran (11.5 g, 44 mmol) was dissolved in 400 mL anhydrous acetonitrile and to the reaction were benzyl bromide (13 mL, 110 mmol), anhydrous potassium carbonate (ground) (16 g, 116 mmol), and a catalytic amount of KI added and the mixture was then heated to 85° C. for 48 h.

The solvent was removed in vacuo, the remains were taken into a 2M solution of $NH_3$ and then extracted twice with ether. The combined ether portions were treated with brine, dried ($MgSO_4$), filtered, and the solvent removed in vacuo to give the crude residue. Chromatography on silica (eluent: $CH_2Cl_2$) gave 15 g (78% yield) of the title compound as a clear oil. $[\alpha]^{21}_D$=−15.5° (C=0.1, CHCl3). GC-MS (70 eV) M=437 (15%).

c) (R)-3-(N,N-Dibenzylamino)-8-fluoro-5-methoxy-3,4-dihydro-2H-1-benzopyran (R)-8-Bromo-3-(N,N-dibenzylamino)-5-methoxy-3,4-dihydro-2H-1-benzopyran (4.35 g, 9.9 mmol) was dissolved in 45 mL of anhydrous THF and cooled to −78° C. To this was a 1.6M n-BuLi solution (6.8 mL, 10.9 mmol) added dropwise and the mixture was allowed to stir at −78° C. for 1 h. N-Fluorobenzenesulfonimide (3.8 g, 11.9 mmol), dissolved in 30 mL anhydrous THF, was added dropwise over 45 min and allowed to stir at −78° C. for 1 h. The reaction was stopped by adding 3 mL saturated $NH_4Cl$ followed by 9 mL of a solution comprised of 2 g of $NH_2OH \times HCl$ and 8 g of $Na_2CO_3$ in 100 mL of $H_2O$ and allowing the reaction to warm to room temperature. A 2M $NH_3$ solution was added and the reaction was extracted twice with ether, treated with brine, dried ($Na_2SO_4$), filtered, and evaporated in vacuo to give the crude product. Purification of the 8-fluoro (desired) from the 8-hydrogen (15 %) compound was carried out by a crude chromatography (eluent: 25% $CH_2Cl_2$/hexane) to give 1.78 g. The crude product was rechromatographed on silica (eluent: 3% acetone/hexane) to give 1.50 g (40% yield) of the title compound as a clear oil. $[\alpha]^{21}_D$=−112.1° (C=0.1, CHCl3). GC-MS (70 eV) M=377 (37%).

d) (R)-3-Amino-8-fluoro-5-methoxy-3,4-dihydro-2H-1-benzopyran (R)-3-(N,N-Dibenzylamino)-8-fluoro-5-methoxy-3,4-dihydro-2H-1-benzopyran (13.0 g, 34.4 mmol) was dissolved in 265 mL methanol and 115 mL THF. To this was 10% Pd/C (4 g) and ammonium formate (51.5 g, 0.817 mol) added. The reaction was heated to 50° C. for 2.5 h. The reaction was filtered and the solvent was removed in vacuo, the remains were taken into a 2M solution of NaOH and then extracted twice with ether. The combined ether portions were treated with brine, dried ($Na_2SO_4$), filtered, and the solvent removed in vacuo to give 6.2 g (91% yield) of the title compound as a clear oil. $[\alpha]^{21}_D$=−15.3° (C=1, CHCl3). GC-MS (70 eV) M=197 (51%).

Preparation 2

(R)-8-Fluoro-3-(N-isopropyl-N-propylamino)-5-trifluoromethylsulfonyloxy-3,4-dihydro-2H-1-benzopyran a) (R)-8-Bromo-3-(N-isopropylamino)-5-methoxy-3,4-dihydro-2H-1-benzopyran (R)-3-(N-Isopropylamino)-5-methoxy-3,4-dihydro-2H-1-benzopyran (4.02 g, 18.2 mmol; prepared as described in WO93/07135) and anhydrous sodium acetate were dissolved in acetic acid (80 mL). To the stirred mixture was bromine (0.93 mL, 18.2 mmol) dissolved in acetic acid (40 mL) added dropwise under 1.5 h.

The solvent was removed in vacuo, taken into a 2M NaOH solution and extracted twice with diethyl ether. The combined ether portions were treated with brine, dried ($Na_2SO_4$), filtered, and the solvent was removed in vacuo to give the crude residue. The hydrochloride salt was made by dissolving the pure base in diethyl ether and adding an excess of an ethereal HCl solution to give a white solid. The salt was recrystallized twice from ethanol/diethyl ether to give 3.8 g (62% yield). p: 257–8° C. $[\alpha]^{21}_D$=−97.7° (C=0.1, CHCl3). The free base was made from the hydrochloride salt to give an oil. GC- MS (70 eV) M=301 (100%).

b) (R)-8-Bromo-3-(N-isopropyl-N-propylamino)-5methoxy-3,4-dihydro-2H-1-benzopyran (R)-8-Bromo-3-(N-isopropylamino)-5-methoxy-3,4-dihydro-2H-1-benzopyran (3.8 g, 11.3 mmol) was dissolved in anhydrous methanol (80 mL) and to this was propanal (8.1 mL, 0.113 mol) added. The reaction was cooled (ice-bath) then sodium cyanoborohydride (1.3 g, 20.3 mmol) was added, the pH was adjusted to 5, and the reaction was allowed to stir at room temperature overnight.

The solvent was removed in vacuo, the remains were taken into a 1M solution of $Na_2CO_3$ and then extracted twice with diethyl ether. The combined ether portions were treated with brine, dried ($Na_2SO_4$). filtered, and the solvent removed in vacuo to give the crude residue. Chromatography on silica (eluent: 7% ethyl acetate/hexane) gave 3.75 g (97% yield) of the title compound as a clear oil. $[\alpha]^{21}_D$= 82.5° (C=0.1, CHCl3). GC-MS (70 eV) M=343 (29%).

The hydrochloride salt was made by dissolving the base in diethyl ether and dropping an excess of an ethereal HCl solution. The salt was recrystallized from ethanol/diethyl ether to give a white solid. Mp: 177–9° C.

c) (R)-8-Fluoro-3-(N-isopropyl-N-propylamino)-5-methoxy-3,4-dihydro-2H-1-benzopyran (R)-8-Bromo-3(N-isopropyl-N-propylamino)-5-methoxy-3,4-dihydro-2H-1-benzopyran (2.3 g, 6.72 mmol) was dissolved in anhydrous THF (25 mL) and cooled to −78° C. To this was a 1.6M n-BuLi solution (4.83 mL, 7.73 mmol) added dropwise and allowed to stir at −78° C. for 1 h. N-Fluorobenzenesulfonimide (2.55 g, 8.06 mmol), dissolved in anhydrous THF (15 mL), was added dropwise under 20–30 min and allowed to stir at −78° C. for 4 h. The reaction was stopped by adding 1 mL of a saturated aqueous $NH_4Cl$ solution followed by 3 mL of a solution comprised of 2 g of $NH_2OH \times HCl$ and 8 g of $Na_2CO_3$ in 100 mL of $H_2O$ and allowing the reaction to warm to room temperature. A 2M $NH_3$ solution was added and the reaction was extracted, twice, with diethyl ether, treated with brine, dried ($Na_2SO_4$), filtered, and evaporated in vacuo to give the crude product.

Chromatography on silica (eluent: chloroform) gave 1.0 g (53% yield) of the title compound as a clear oil. $[\alpha]^{21}_D=$ 89.2° (C=0.1, CHCl3). GC-MS (70 eV) M=281 (32%).

The hydrochloride salt was made by dissolving the pure base in diethyl ether and dropping an excess of an ethereal HCl solution to give a white solid (sinters at 80° C.).

d) (R)-8-Fluoro-3-(N-isopropyl-N-propylamino)-5-hydroxy-3,4-dihydro-2H-1-benzopyran (R)-8-Fluoro-3-(N-isopropyl-N-propylamino)-5-methoxy-3,4-dihydro-2H-1-benzopyran hydrochloride (1.03 g, 3.24 mmol) was dissolved in anhydrous $CH_2Cl_2$ (30 mL) and cooled to −40° C. To the solution was $BBr_3$ (0.77 mL, 8.1 mmol), dissolved in anhydrous $CH_2Cl_2$ (5 mL) added dropwise. The cooling-bath was removed and after 3 h at room temperature the reaction was complete.

The reaction was poured out onto an ice/2M $NH_3$ solution and the mixture was extracted, twice, with diethyl ether. The combined ether portions were treated with brine, dried ($Na_2SO_4$), filtered, and the solvent removed in vacuo to give the crude residue.

Chromatography on silica (eluent: 20% ethyl acetate/hexane) gave 0.84 g (97% yield) of the title compound as a clear oil. $[\alpha]^{21}_D=-94.2°$ (C=0.1, CHCl3). GC-MS (70 eV) M=267 (26%).

The hydrochloride salt was made by dissolving the pure base in diethyl ether and dropping an excess of an ethereal HCl solution. The salt was recrystallized from $CHCl_3$/diethyl ether/ethyl acetate to give a white solid. Mp: 220–2° C.

e) (R)-8-Fluoro-3-(N-isopropyl-N-propylamino)-5-trifluoromethylsulfonyloxy-3,4-dihydro-2H-1-benzopyran (R)-8-Fluoro-3-(N-isopropyl-N-propylamnino)-5-hydroxy-3,4-dihydro-2H-1-benzopyran (0.71 g, 2.66 mmol) and collidine (0.49 mL, 3.72 mmol) were dissolved in anhydrous $CH_2Cl_2$ (25 mL) and cooled to −40° C. Trifluoromethanesulfonic anhydride (0.54 mL, 3.2 mmol) was added dropwise and allowed to warm to ambient temperature, and after coming to 0° C. the reaction was done. The reaction was diluted with $CH_2Cl_2$ and washed with a saturated aqueous $NaHCO_3$ solution, dried ($MgSO_4$), filtered, and evaporated in vacuo to give a crude residue. Chromatography on silica (eluent $CH_2Cl_2$) gave 0.82 g (77% yield) of the title compound as a clear oil. $[\alpha]^{21}_D=-85.5°$ (C=0.1, CHCl3). GC-MS (70 eV) M=399 (6%).

EXAMPLE 1

(R)-3-(N-Cyclopentyl-N-n-propylamino)-8-fluoro-5-N-methylcarbamoyl-3,4-dihydro-2H-1-benzopyran a) (R)-3-N-Cyclopentylamino-8-fluoro-5-methoxy-3,4-dihydro-2H-1-benzopyran (R)-3-Amino-8-fluoro-5-methoxy-3,4-dihydro-2H-1-benzopyran (1.5 g, 7.6 mmol), acetic acid (0.45 g, 7.6 mmol), and cyclopentanone (2.5 g, 3 mmol) were dissolved in 30 ml of methanol. With stirring, sodiumcyanoborohydride (0.8 g, 13 mmol) was added in portions under a few minutes. Stirring was continued for 2 hours. A GC sample showed 100% of a new product. The solvent was evaporated and water, 2M $NH_3$ and EtOAc were added. The organic layer was separated and washed with water. The layer was dried with $Na_2SO_4$ and evaporated to give 1.3 g (64% yield) of a colourless oil. GC/MS with the molecular peak of 265 confirmed the title compound.

b) (R)-3-(N-Cyclopentyl-N-n-propylamino)-8-fluoro-5-methoxy-3,4-dihydro-2H-1-benzopyran (R)-3-N-Cyclopentylamino-8-fluoro-5-methoxy-3,4-dihydro-2H-1-benzopyran (1.3 g, 5 mmol), acetic acid (0.3 g, 5 mmol) and propionaldehyde (1.5 g, 25 mmol) were dissolved in 30 ml of methanol. With stirring, sodiumcyanoborohydride (0.8 g, 13 mmol) was added in portions over a few minutes and stirring was continued. After 3 hours a GC sample showed 100% of a new product. The solvent was evaporated and water, 2 molar $NH_3$ and EtOAc were added. The organic layer was separated and washed neutral with water. The layer was dried with $Na_2SO_4$ and evaporated to give 1 g (65% yield) of a colourless oil. GC/MS with the molecular peak of 307 confirmed the title compound.

c) (R)-3-(N-Cyclopentyl-N-n-propylamino)-8-fluoro-5-hydroxy-3,4-dihydro-2H-1-benzopyran (R)-3-(N-Cyclopentyl-N-n-propylamino)-8-fluoro-5-methoxy-3,4-dihydro-2H-1-benzopyran (1 g, 5 mmol) was dissolved in 25 ml of $CH_2Cl_2$. An excess of etheric HCl was added to form the HCl salt. A solution of $BBr_3$ (4 g, 15 mmol) in 10 ml of $CH_2Cl_2$ was prepared and added dropwise under 10 minutes with stirring (ice-bath). The reaction mixture was allowed to reach room temperature during continued stirring for 6 hours and the mixture was poured out into ice water and made alkaline by adding ammonia. The organic layer was separated, dried with $Na_2SO_4$ and evaporated to afford a dark brown oil. Chromatography ($SiO_2$, di-isopropyl ether and hexane 1+1) afforded 1.1 g of an colourless oil. The HCl salt was prepared from the base and etheric HCl and recystallized from acetonitrile to give 0.85 g (52% yield). Mp 220–221° C.

d) (R)-3-(N-Cyclopentyl-N-n-propylamino)-8-fluoro-5-trifuoromethylsulfonyloxy-3,4-dihydro-2H-1-benzopyran (R)-3-(N-Cyclopentyl-N-n-propylamino)-8-fluoro-5-hydroxy-3,4-dihydro-2H-1-benzopyran (0.7 g, 3 mmol) was dissolved in 25 ml of $CH_2Cl_2$ and triethylamine (0.3 g, 3 mmol) was added. The solution of trifluoromethanesulfonic anhydride (1 g, 4 mmol) in 5 ml of $CH_2Cl_2$ was added dropwise over 10 min (−20° C.). Stirring was continued for 1 hour. The reaction mixture was poured out into ice water and the pH was adjusted to 8 by addition of ammonia and the mixture extracted by ether. The organic layer was separated, dried with $Na_2SO_4$ and evaporated to afford a brown oil. Chromatography ($SiO_2$, $CH_2Cl_2$ +hexane, 1+3) afforded 0.5 g (44% yield) of a colourless oil. GC/MS with the molecular peak of 425 confirmed the title compound.

e) (R)-3-(N-Cyclopentyl-N-n-propylamino)-8-fluoro-5-N-methylcarbamoyl-3,4-dihydro-2H-1-benzopyran (R)-3-(N-Cyclopentyl-N-n-propylamino-8-fluoro-5-trifluoromethylsulfonyloxy-3,4-dihydro-2H-1-benzopyran (0.5 g, $_1$ mmol) was dissolved in 15 ml of 1,4-dioxane. Palladium II acetate (10 mg), 1,3-bis (diphenylphosphino)-propane (20 mg), and methylamine (0.15 g, 5 mmol) were added and the mixture was stirred in carbon monoxide atmosphere over night at 70° C. Evaporation and chromatography ($SiO_2$, diethyl ether +hexane 1+3) afforded the final compound as a colourless oil. The HCl salt was prepared to give 0.24 g (65% yield) of white crystals. Mp 108° G.

EXAMPLE 2

(R)-8-Fluoro-3-(N-isopropyl-N-n-propylamino)-5carbamoyl-3,4-dihydro-2H-1-benzopyran a) Methyl (R)-8-fluoro-3-N-isopropyl-N-n-propylamino)-3,4-dihydro-2H-1-benzopyran-5-carboxylate (R)-8-Fluoro-3-(N-isopropyl-N-n-propylamino)-5-trifluoromethanesulfonyloxy-3,4-dihydro-2H-1-benzopyran (2.4 g, 6.0 mmol), triethylamine (1.3 g, 12.9 mmol), 1,3-bis(diphenylphosphino)propane (95 mg, catalytic amount), palladium(II)acetate (48 mg, catalytic amount) and DMF/MeOH (30 mL, 3:1) were mixed in a 50 mL three necked round bottom flask. The flask was evacuated followed by the inlet of CO (repeated two times). The reaction mixture was stirred at 70° C. for 7.5 hours. The solvent was removed in vacuo and the residue was dissolved in diethyl ether/sat. NaHCO$_3$. The layers were separated and the water phase was extracted once with ether. The combined ether layers were dried (MgSO$_4$) and the solvent was removed in vacuo to give a crude which was purified by flash chromatography (SiO$_2$, hexane/EtOAC, 9:1) to give 1.3 g of the title compound (71% yield).

b) (R)-8-Fluoro-3-(N-isopropyl-N-n-propylamino)-5-carbamoyl-3,4-dihydro-2H-1-benzopyran Methyl (R)-Fluoro-3-(N-isopropyl-N-n-propylamino)-3,4-dihydro-2H-1-benzopyran-5-carboxylate (1.3 g, 4.2 mmol) and KOH (0.52 g, 8.4 mmol) were mixed in methanol (6 mL) and refluxed for 2.5 hours. The solvent was removed in vacuo. The residue was dissolved in water and made acidic by the addition of 2M HCl. The solvent was removed in vacuo. The residue was dissolved in SOCl$_2$ (30 mL) and refluxed for 2.5 hours. The solvent was removed in vacuo. The residue was dissolved in CH$_2$Cl$_2$ and the solvent was removed in vacuo again (repeated three times in order to remove the excess of SOCl$_2$). The residue was then dissolved in diethyl ether (50 mL). The solution was cooled to −30° C. before NH$_3$ (g) was bubbled through it. Water was added, the layers were separated and the water-phase was extracted with ether. The combined ether layers were dried (K$_2$CO$_3$) and the solvent was removed in vacuo to give a crude preparation which was purified by flash chromatography (SiO$_2$, EtOAc/hexane, 1:1) to give 1.0 g of the title compound (yield 80%). Recrystallization from EtOAc/hexane gave crystals with Mp: 139–140° C.

EXAMPLE 3

(R)-3-(N-tert-Butyl-N-n-propylamino)-5carbamoyl-8-fluoro-3,4dihydro-2H-1-benzopyran a) (R)-8-Fluoro-5-methoxy-3-[N-(4-methoxybenzylidene)-amino]-3,4-dihydro-2H-1-benzopyran (R)-3-Amino-8-fluoro-5-methoxy-3,4-dihydro-2H-1-benzopyran (7.85 g, 39.8 mmol), 4-methoxybenzaldehyde (5.42 g, 39.8 mmol), anhydrous potassium carbonate (10.1 g) and absolute EtOH (200 mL) were stirred over night at reflux temperature. The solvent was evaporated in vacuo and ether (500 mL) was added. After stirring for 15 min the salt was filtered off and the solution was concentrated in vacuo to give an off-white solid (12.4 g). Recrystallization from i-Pr$_2$O- hexane gave 10.8 g (86% yield) of the title compound as colourless needles. Mp: 96.8–97.3° C. [α]$^{21}_D$+ 20.1° (C=1; CHCl3). GC-MS (70 eV) M=315 (58%).

b) (R)-8-Fluoro-3-hydroxylamino-5methoxy-3,4-dihydro-2H-1-benzopyran

3-Chloroperoxybenzoic acid (85%; 7.6 g, 37.6 mmol) was added in portions to a stirred and cooled solution (+4° C.) of (R)-8-fluoro-5-methoxy-3-[N-(4-methoxybenzylidene)-amino]-3,4-dihydro-2H-1-benzopyran (10.8 g, 34 mmol) and methylene chloride (65 mL). The mixture was stirred over night at room temperature. Precipitated 3-chlorobenzoic add was filtered off and the dear yellow filtrate was concentrated in vacuo. The oily residue was taken up in a solution of hydroxylamine hydrochloride (2.83 g, 40.8 mmol) and anhydrous methanol (60 mL) and the resulting solution was stirred at room temperature for 2 h. The solvent was evaporated to give a thick orange oil. Water was added to the oil, pH was adjusted to 8–9 with saturated aqueous Na$_2$CO$_3$ and the mixture was washed with ether (3×150 mL). The organic phases were combined, washed with brine, dried (Na$_2$SO$_4$), filtered and concentrated in vacuo. The crude product was flash chromatographed on silica with EtOAc (15 to 50%) in hexane as eluent. The resulting impure product was flash chromatographed a second time on silica with EtOH- CHCl$_3$ (1:99) as eluent to give 6.45 g (89% yield) of the title compound as a colourless crystalline solid. Mp: 111–113° C. [α]$^{21}_D$=+66.4° (C=1.3; CHCl$_3$). GC-MS (70 eV) M=213 (56%).

c) (R)-3-tert-Butylamino-8-fluoro-5-methoxy-3,4-dihydro-2H-1-benzopyran (R)-8-Fluoro-3-hydroxylamino-5-methoxy-3,4-dihydro-2H-1-benzopyran (6.30 g, 29.6 mmol), anhydrous sodium sulfate (20 g) and acetone (500 mL) were refluxed under nitrogen for 4 days until TLC indicated a complete reaction. The salt was filtered off, ether (300 mL) was added to the filtrate and the solution, still containing finely suspended salt, was filtered through a sintered glass filter (grade 4). The clear filtrate was concentrated in vacuo. Dry (sieves 3 Å) benzene (50 mL) was added and the resulting solution was concentrated in vacuo (finally on the pump). The glassy residue was dissolved in dry (sieves 3 Å) benzene (150 mL) under nitrogen and the solution was cooled on an ice-bath (+4° C.). MeMgBr in Et$_2$O (3.0M; 32.0 mL, 96 mmol) was added to the stirred solution above at a rate that kept the internal temperature below +5° C. (the reaction is exothermic). After the addition was complete (30 min) the solution was stirred at +4° C. for 0.5 h. The cooling bath was taken away and 15 min later the solution was poured on saturated NaHCO$_3$ and ice (300 mL total). The mixture was washed repeatedly with ether (3×150 mL). The organic phases were combined, washed with brine, dried (Na$_2$SO$_4$), filtered and concentrated in vacuo. Flash chromatography on silica [eluent EtOAc (2 and 10%) in CHCl$_3$] gave 2.9 g. of the tert -butyl hydroxylamine derivative. The latter was dissolved in CS$_2$ (100 mL) under nitrogen and the solution was stirred at room temperature for 4.5 h. The solvent was evaporated in vacuo to give an orange oil. Acetone (approx. 50 mL) was added and the solution was stirred for a short time (15 min) at room temperature (to precipitate elemental sulfur), then filtered and concentrated to give an oil. Flash chromatography on silica [eluent: EtOAc (10 to 25%) in hexane] gave 2.34 g (31% total yield) of the title compound as a yellow oil. [α]$^{21}_D$=+82.8° (C=1; CHCl3). GC-MS (70 eV) M=253 (53%).

d) (R)-3-(N-tert-Butyl-N-n-propylamino)-8-fluoro-5-methoxy-3,4-dihydro-2H-1-benzopyran (R)-3-tert-Butylamino-8fluoro-5-methoxy-3,4-dihydro-2H-1-benzopyran (2.20 g, 8.7 mmol), allyl bromide (7.5 mL, 87 mmol), finely ground anhydrous potassium carbonate (6.0 g, 43 mmol) and dry DMF (6.0 mL) were stirred under nitrogen at 65° C. After 70 h GC-analysis indicated partial conversion of the starting material (67% product vs. 30% starting material). At this stage the reaction was interrupted. The salt was sucked off, washed with small portions of DMF and the clear filtrate was concentrated. The oil thus obtained was partitioned between saturated aqueous Na$_2$CO$_3$ and diethyl ether (4×70 mL). The organic phases were combined, washed with brine, dried (MgSO$_4$), filtered and concentrated in vacuo. Flash chromatograpy on silica [eluent: acetone (2 and 15%) in hexane] gave 0.80 g of starting material and 1.47 g (87% yield based on recovered starting material) of the allylated product as a colourless oil. [α]$^{21}_D$=−77.6° (C=0.8, CHCl$_3$). GC-MS (70 eV) M=293 (40%). The allylated product (1.30 g) was mixed with DMF (50 mL) and 5% Rh on alumina (0.090 g) and hydrogenated at ambient pressure and temperature (21° C.). After 5 h the reaction was complete according to GC and TLC. The catalyst was filtered off on Celite, the pad was washed with small portions of DMF and the filtrate was concentrated in vacuo. Flash chromatography on silica of the crude product [eluent: EtOAc (0 and 3%) in $CH_2Cl_2$] gave 1.27 g (97% yield) of the saturated compound. GC-MS (70 eV) M=295 (28%). $[\alpha]^{21}_D$ (base)=−83.4° (C=0.9; CHCl3).

The base was dissolved in dry diethyl ether, the solution was cooled on an ice bath and an excess of ethereal HCl was added to the stirred solution. The salt was filtered off, washed with dry diethyl ether and dried in vacuo at 50° C. to give 1.39 g (98% yield) of the title compound, as white crystals. Mp: 175–176° C.

e) (R)-3-(N-tert-Butyl-N-n-propylamino)-8-fluoro-5-hydroxy-3,4-dihydro-2H-1-benzopyran (R)-3-(N-tert-Butyl-N-n-propylamino)-8-fluoro-5-methoxy-3,4-dihydro-2H-1-benzopyran hydrochloride (1.3 g, 3.9 mmol) in dry methylene chloride (40 mL) under nitrogen was cooled on a dry ice-EtOH bath to −50° C. Boron tribromide (0.75 mL, 7.8 mmol) was added dropwise (in 1 min) to the stirred solution above. Five minutes after the addition of boron tribromide was complete, the dry-ice bath was changed to an ice bath (+4° C.). After stirring for 4 h at the same temperature the solution was poured on ice (100 g) and solid $NaHCO_3$ was added to adjust pH to 8–9. When the ice had melted the mixture was extracted with ether (4×75 mL). The ether extracts were combined, washed with brine, dried ($Na_2SO_4$), filtered and concentrated in vacuo to afford 1.1 g (96% yield) of the title compound as a pale yellow oil. $[\alpha]^{21}_D$=−91.7° (C=1.0; CHCl3). GC-MS (70 eV) M=281 (6%).

f) (R)-3-(N-tert-Butyl-N-n-propylamino)-8-fluoro-5-trifluoromethylsulfonyloxy-3,4-dihydro-2H-1-benzopyran (R)-3-(N-tert-Butyl-N-n-propylamino)-8-fluoro-5-hydroxy-3,4-dihydro-2H-1-benzopyran (1.0 g, 3.6 mmol) and 2,4,6-collidine (0.52 mL, 3.9 mmol) were dissolved in anhydrous methylene chloride (40 mL) and cooled to −30° C. Trifluoromethanesulfonic anhydride (0.66 mL, 3.9 mmol) dissolved in anhydrous methylene chloride (10 mL) was added dropwise during 20 min. The solution was allowed to warm to ambient temperature and after coming to 0° C. the reaction was done. The reaction was diluted with methylene chloride and washed with saturated aqueous $NaHCO_3$ (50 mL). The aqueous phase was re-extracted with ether (2×40 mL). The combined organic phases were dried ($MgSO_4$), filtered, and concentrated in vacuo to give a crude residue. Flash chromatography on silica [eluent: EtOAc-hexane (3:97)] gave 1.40 g (95% yield) of the title compound as a colourless oil. $[\alpha]^{21}_D$=−73.7° (C=1.1; CHCl3). GC-MS (70 eV) M=413 (1%).

g) Methyl (R)-3-(N-tert-Butyl-N-n-propylamino)-8-fluoro-3,4-dihydro-2H-1-benzopyran-5-carboxylate (R)-3-(N-tert-Butyl-N-n-propylamino)-8fluoro-5-trifluoromethylsulfonyloxy-3,4-dihydro-2H-1-benzopyran (1.4 g, 3.3 mmol) and triethylamine (1.0 mL, 7.4 mmol) were dissolved in a solution of DMF/MeOH (6:2; 30 mL) and then degassed followed by the inlet of carbon monoxide (4×). With a slight positive pressure of carbon monoxide, palladium(II)-acetate (0.030 g) and 1,3-bis (diphenylphosphino)propane (0.060 g) were added and the reaction mixture was degassed and subjected to carbon monoxide once again. The reaction was heated to 70° C. (oil-bath temperature) under carbon monoxide atmosphere with vigorous stirring for 12 h. GC indicating an incomplete reaction (68% product vs. 21% starting material), the solution was cooled and then filtered through Celite. More palladium(II)-acetate (0.030 g) and 1,3-bis (diphenylphosphino)propane (0.060 g) were added and the reaction was resumed as described above. After another 3 h GC indicated a slight improvement of the ratio (77% vs. 12%) and the reaction was allowed to cool. The following day the solvent was removed in vacuo. The remaining red-brown oil was taken into saturated aqueous $NaHCO_3$ and then extracted with EtOAc (3×50 mL). The combined organic phases were washed with brine, dried ($MgSO_4$), filtered and concentrated in vacuo to give the crude ester. Flash chromatography on silica [eluent: EtOAc (15 and 30%) in hexane] gave 0.178 g of starting material and 0.842 g (89% yield based on recovered starting material) of the title compound as a clear oil. $[\alpha]^{21}_D$=−121.1° (C=0.9; CHCl3). GC-MS (70 eV) M=323 (14%).

h) (R)-3-(N-tert-Butyl-N-n-propylamino)-5-carbamoyl-8-fluoro-3,4-dihydro-2H-1-benzopyran Methyl (R)-3-(N-tert-butyl-N-n-propylamino)-8-fluoro3,4-dihydro-2H-1-benzopyran-5-carboxylate (0.84 g, 2.6 mmol), methanol (10 mL) and 1.7M aqueous NaOH (3.0 mL, 5.2 mmol) were refluxed for 3 h. The clear solution was cooled, the methanol was stripped, the aqueous remains were washed twice with ether-hexane (1:1), then acidified with 2M HCl (pH≦2). The water was evaporated in vacuo and the remaining salt was dried in vacuum at 50° C. for 2 h. Dry methylene chloride (20 mL) and thionyl chloride (3.0 mL, 41 mmol) were added, the mixture refluxed under nitrogen for 11 h. The volatiles were evaporated, more dry methylene chloride was added and evaporated. This was repeated once. The crude acid chloride was dissolved (suspended) in dry methylene chloride (50 mL) and added dropwise to stirred concentrated aqueous ammonia (40 mL) cooled on an ice bath. The mixture was allowed to warm to ambient temperature, the organic phase was separated, and the aqueous phase was washed with methylene chloride (100 mL) and ether (50 mL). The organic portions were combined, dried ($MgSO_4$), filtered and concentrated to give the crude amide. Flash chromatography on silica [eluent: EtOAc-hexane (4:5)]) gave 0.73 g (91% yield) of (R)-3-(N-tert-butyl-N-propylamino)-8-fluoro-3,4-dihydro-2H-1-benzopyran-5-carboxamide as a solid. Mp: 70–75° C. $[\alpha]^{21}_D$=−132.4° (C=1.0; CHCl3). GC-MS (70 eV) M=308 (3%).

The base was dissolved in dry ether, the solution was cooled on a dry-ice bath (−20° C.) and an excess of ethereal HCl was added to the stirred solution. The salt was filtered off, washed with dry ether and dried in vacuo at 50° C. to give 0.78 g (96% yield) of the hydrochloride salt as white crystals. Mp: 120° C. sinters.

EXAMPLE 4

(R)-5-Carbamoyl-3-(N,N-dicyclobutylamino)-8-fluoro-3,4-dihydro-2H-1-benzopyran a) (R)-3-(N-Cyclobutylamino)-8-fluoro-5-methoxy-3,4-dihydro-2H-1-benzopyran and (R)-3-(N,N-Dicyclobutylamino)-8-fluoro-5-methoxy-3,4-dihydro-2H-1-benzopyran (R)-3-Amino-8-fluoro-5-methoxy-3,4-dihydro-2H-1-benzopyran (1.67 g, 8.47 mmol) was dissolved in anhydrous methanol (20 mL) and to this was cyclobutanone (5.0 g, 71.3 mmol) added. The reaction was cooled (ice-bath) then sodium cyanoborohydride (0.96 g, 15.3 mmol) was added and the reaction was allowed to stir at room temperature overnight. After 24 h the pH was adjusted to 4–5 with acetic acid and the reaction was allowed to stir for one more day.

The solvent was removed in vacuo, the remains were taken into a 2M solution of $NH_3$ and then extracted thrice with diethyl ether. The combined ether portions were dried ($Na_2SO_4$), filtered, and the solvent removed in vacuo to give the crude residue. Chromatography on silica (eluent: 15% ethyl acetate/hexane for dialkylated product followed by ethyl acetate for monoalkylated product) gave 1.01 g (48% yield) of the monoalkylated title compound as a clear oil [GC-MS (70 eV) M=251 (6%)]. and 0.71 g (27% yield) of the dialkylated title compound as a clear oil. $[\alpha]^{21}_D = -101.0°$ (C=0.1; $CHCl_3$). GC-MS (70 eV) M=305 (3%).

b) (R)-8-Fluoro-3-(N,N-dicyclobutylamino)-5-hydroxy-3,4dihydro-2H-1-benzopyran

8-Fluoro-3-(N,N-dicyclobutylamino)-5-methoxy-3,4-dihydro-2H-1-benzopyran hydrochloride (0.77 g, 2.26 mmol) was dissolved in anhydrous $CH2Cl_2$ (20 mL) and cooled to −40° C. To the solution was $BBr_3$ (0.54 mL, 5.7 mmol), dissolved in anhydrous $CH_2Cl_2$ (3 mL) added dropwise. The cooling-bath was removed and after 2 h at room temperature the reaction was complete.

The reaction was poured out onto an ice/2M $NH_3$ solution and the mixture was extracted, twice, with diethyl ether. The combined ether portions were dried ($MgSO_4$), filtered, and the solvent removed in vacuo to give the crude residue.

Chromatography on silica (eluent: 50% ethyl acetate/hexane) gave 0.58 g (89% yield) of the title compound as a white solid. Mp: 170–2° C. $[\alpha]^{21}_D = -114.4°$ (C=0.1; CHCl3). GC-MS (70 eV) M=291 (2%).

c) (R)-3-(N,N-Dicyclobutylamino)-8-fluoro-5-trifluoromethylsulfonyloxy-3,4-dihydro-2H-1-benzopyran (R)-3-(N,N-Dicyclobutylamino)-8-fluoro-5-hydroxy-3,4-dihydro-2H-1-benzopyran (0.59 g, 2.02 mmol) and collidine (0.37 mL, 2.8 mmol) were dissolved in anhydrous $CH_2Cl_2$ (40 mL) and cooled to −40° C. Trifluoromethanesulfonic anhydride (0.41 mL, 2.4 mmol) was added dropwise and allowed to warm to ambient temperature, and after coming to 0° C. the reaction was done. The reaction was diluted with $CH_2Cl_2$ and washed with a saturated aqueous $NaHCO_3$ solution, dried ($MgSO_4$), filtered, and evaporated in vacuo to give a crude residue. Chromatography on silica (eluent $CH_2Cl_2$) gave 0.84 g (99% yield) of the title compound as a clear oil. $[\alpha]^{21}_D = -90.9°$ (C=0.1; CHCl3). GC-MS (70 eV) M=423 (3%).

d) Methyl (R)-3-(N,N-Dicyclobutylamino)-8-fluoro-3,4-dihydro-2H-1-benzopyran-5-carboxylate (R)-3-(N,N-Dicyclobutylamino)-8-fluoro-5-trifluoromethylsulfonyloxy-3,4-dihydro-2H-1-benzopyran (0.82 g, 1.94 mmol) was dissolved in a solution of DMF/methanol (6:2, 15 mL) and then degassed followed by the inlet of carbon monoxide (×3). With a slight positive pressure of carbon monoxide, palladium(II)-acetate (14 mg), 1,3-bis(diphenylphosphino)propane (25 mg) and triethylamine (0.60 mL, 4.3 mmol) were added and the reaction mixture was degassed and subjected to carbon monoxide once again. The reaction was heated to 70° C. under carbon monoxide atmosphere with vigorous stirring for 5.5 h.

The reaction was allowed to cool and the solvent was removed in vacuo. The remains were taken into a 2M solution of $NH_3$ and then extracted, twice, with diethyl ether. The combined ether portions were dried ($MgSO_4$), filtered, and the solvent removed in vacuo to give the crude residue. Chromatography on silica (eluent: 12.5% ethyl acetate/hexane) gave 501 mg (78% yield) of the title compound as a clear oil. $[\alpha]^{21}_D = -138.2°$ (C=0.1; CHCl3). GC-MS (70 eV) M=333 (4%).

e) (R)-5-Carbamoyl-3-(N,N-dicyclobutylamino)-8-fluoro-3,4-dihydro-2H-1-benzopyran Methyl (R)-3-(N,N-dicyclobutylamino)-8-fluoro-3,4-dihydro-2H-1-benzopyran-5-carboxylate (490 mg, 1.47 mmol) was refluxed with a 6M solution of HCl (20 mL) for 3.5 h. The solution was cooled, concentrated to dryness in vacuo and anhydrous toluene was added and the solvent was removed in vacuo (×4).

To the white solid was thionyl chloride (15 mL) added and the solution was allowed to stir at room temperature overnight. The excess thionyl chloride was removed in vacuo, anhydrous toluene added and the solvent removed in vacuo.

The acid chloride was dissolved in $CH_2Cl_2$ (20 mL) and added dropwise to a cooled solution (ice-bath) of concentrated $NH_3$ (20 mL). The reaction was allowed to stir at room temperature for 30 min. The $CH_2Cl_2$ phase was separated and the aqueous portion was re-extracted with $CH_2Cl_2$ (×3). The combined $CH_2Cl_2$ portions were dried (MgSO4), filtered, and evaporated in vacuo to give the crude residue. Chromatography on silica (eluent: ethyl acetate) gave 430 mg (92% yield) of a white solid. Mp: 141.2–142.2° C. $[\alpha]^{21}_D = -151.5°$ (C=0.1; CHCl3). GC-MS (70 eV) M=318 (3%).

The hydrochloride salt was made by dissolving the pure base in ether and adding dropwise an excess of an ethereal HCl solution. The salt was washed with diethyl ether to give a white solid. Mp: 120° C. sinters.

EXAMPLE 5

(R)-5-Carbamoyl-3-(N-cyclobutyl-N-n-propylamino)-8-fluoro-3,4-dihydro-2H-1-benzopyran a) (R)-3-(N-Cyclobutyl-N-n-propylamino)-8-fluoro-5-methoxy-3,4-dihydro-2H-1-benzopyran (R)-3-(N-Cyclobutylamino)-8-fluoro-5-methoxy-3,4-dihydro-2H-1-benzopyran (1.01 g, 4.02 mmol) was dissolved in anhydrous methanol (20 mL) and to this was n-propionaldehyde (3.0 mL, 40.2 mmol) added. After 1 h the reaction was cooled (ice-bath) then sodium cyanoborohydride (0.46 g, 7.24 mmol) was added, the pH was adjusted to 4–5 with acetic acid and the reaction was allowed to stir at room temperature over the weekend. The solvent was removed in vacuo, the remains were taken into a 2M solution of $NH_3$ and then extracted thrice with diethyl ether. The combined ether portions were dried ($MgSO_4$), filtered, and the solvent removed in vacuo to give the crude residue. Chromatography on silica (eluent 11% ethyl acetate/hexane) gave 0.95 g (80% yield) of the title compound as a clear oil. $[\alpha]^{21}_D = -95.4°$ (C=0.1; CHCl3). GC-MS (70 eV) M=293 (1%).

b) (R)-3-(N-Cyclobutyl-N-n-propylamino)-8-fluoro-5-hydroxy-3,4-dihydro-2H-1-benzopyran (R)-3-(N-Cyclobutyl-N-n-propylamino)-8-fluoro-5-methoxy-3,4dihydro-2H-1-benzopyran hydrochloride (1.0 g, 3.03 mmol) was dissolved in anhydrous $CH2Cl_2$ (25 mL) and cooled to −40° C. To the solution was $BBr_3$ (0.72 mL, 7.6 mmol), dissolved in anhydrous $CH_2Cl_2$ (4 mL), added dropwise. The cooling-bath was removed and after 2 h at room temperature the reaction was complete.

The reaction was poured out onto an ice/2M $NH_3$ solution and the $CH_2Cl_2$ portion was separated, the aqueous layer re-extracted, twice, with $CH_2Cl_2$. The combined $CH_2Cl_2$ portions were dried ($MgSO_4$), filtered, and the solvent removed in vacuo to give the crude residue. Chromatography on silica (eluent: 25% ethyl acetate/hexane followed by 50% ethyl acetate/hexane) gave 0.83 g (98% yield) of the title compound as a gum. $[\alpha]^{21}_D = -80.5°$ (C=0.1; CHCl3). GC-MS (70 eV) M=279 (0.2%;

c) (R)-3-(N-Cyclobutyl-N-n-propylamino)-8-fluoro-5-trifluoromethylsulfonyloxy-3,4-dihydro-2H-1-benzopyran (R)-3-(N-Cyclobutyl-N-n-propylamino)-8-fluoro-5-hydroxy-3,4-dihydro-2H-1-benzopyran (0.80 g, 2.86 mmol) and collidine (0.53 mL, 4.0 mmol) were dissolved in anhydrous $CH_2Cl_2$ (30 mL) and cooled to −40° C. Trifluoromethanesulfonic anhydride (0.60 mL, 3.6 mmol) was added dropwise and allowed to warm to ambient temperature, and after coming to 0° C. the reaction was done. The reaction was diluted with $CH_2Cl_2$ and washed with a saturated aqueous $NaHCO_3$ solution, the aqueous was re-extracted, twice, with $CH_2Cl_2$ the combined $CH_2Cl_2$ portions were dried ($MgSO_4$), filtered, and evaporated in vacuo to give a crude residue. Chromatography on silica (eluent: $CH_2Cl_2$) gave 1.01 g (86% yield) of the title compound as a clear oil. $[\alpha]^{21}_D=-78.6°$ (C=0.1; CHCl3). GC-MS (70 eV) M=411 (1%).

d) Methyl (R)-3-(N-Cyclobutyl-N-n-propylamino)-8-fluoro-3,4-dihydro-2H-1-benzopyran-5carboxylate (R)-3-(N-Cyclobutyl-N-n-propylamino)-8-fluoro-5-trifluoromethylsulfonyloxy-3,4dihydro-2H-1-benzopyran (1.00 g, 2.43 mmol) was dissolved in a solution of DMF/methanol (6:2, 20 mL) and then degassed followed by the inlet of carbon monoxide (×3). With a slight positive pressure of carbon monoxide, palladium(II)-acetate (18 mg), 1,3-bis(diphenylphosphino)propane (25 mg) and triethylamine (0.75 mL, 5.3 mmol) were added and the reaction mixture was degassed and subjected to carbon monoxide once again. The reaction was heated to 70° C. under carbon monoxide atmosphere with vigorous stirring for 6 h. The reaction was allowed to cool and the solvent was removed in vacuo. The remains were taken into a 2M solution of $NH_3$ and then extracted, twice, with diethyl ether. The combined ether portions were dried ($MgSO_4$), filtered, and the solvent removed in vacuo to give the crude residue. Chromatography on silica (eluent: 15% ethyl acetate/hexane) gave 0.73 mg (94% yield) of the title compound as a clear oil. $[\alpha]^{21}_D=-130.1°$ (C=0.1; CHCl3). GC-MS (70 eV) M=321 (2%).

e) (R)-5-Carbamoyl-3-(N-cyclobutyl-N-n-propylamino)-8-fluoro-3,4-dihydro-2H-1-benzopyran Methyl (R)-3-(N-cyclobutyl-N-n-propylamino)-8-fluoro-3,4-dihydro-2H-1-benzopyran-5-carboxylate (0.71 mg, 2.21 mmol) was refluxed with a 6M solution of HCl (30 mL) for 3.5 h. The solution was cooled, concentrated to dryness in vacuo and anhydrous toluene was added and the solvent was removed in vacuo (×4).

To the white solid was thionyl chloride (20 mL) added and the solution was allowed to stir at room temperature overnight. The excess thionyl chloride was removed in vacuo, anhydrous toluene added and the solvent removed in vacuo.

The acid chloride was dissolved in $CH_2Cl_2$ (30 mL) and added dropwise to a cooled solution (ice-bath) of concentrated $NH_3$ (30 mL). The reaction was allowed to stir at room temperature for 40 min. The $CH_2Cl_2$ phase was separated and the aqueous portion was re-extracted with $CH_2Cl_2$ (×3). The combined $CH_2Cl_2$ portions were dried (MgSO4), filtered, and evaporated in vacuo to give the crude residue. Chromatography on silica (eluent ethyl acetate) gave 622 mg (92% yield) of a white semi-crystalline solid. A portion was recrystallized from ethyl acetate/hexane to give a feathery white solid. Mp: 107–9° C. $[\alpha]^{21}_D=-133.0°$ (C=0.1; CHCl3). GC-MS (70 eV) M=306 (0.5%).

EXAMPLE 6

(R)-5-Carbamoyl-3-(N-cyclobutyl-N-isopropylamino)-8-fluoro-3,4-dihydro-2H-1-benzopyran a) (R)-8-Fluoro-3-(N-isopropylamino)-5-methoxy-3,4-dihydro-2H-1-benzopyran (R)-3-Amino-8-fluoro-5-methoxy-3,4-dihydro-2H-1-benzopyran (1.62 g, 8.21 mmol) was dissolved in anhydrous methanol (20 mL) and to this was acetone (6.0 mL, 82.1 mmol) added. The reaction was cooled (ice-bath) then sodium cyanoborohydride (0.92 g, 14.8 mmol) was added, the pH was adjusted to 4–5 with acetic acid and the reaction was allowed to stir at room temperature overnight. The solvent was removed in vacuo, the remains were taken into a 2M solution of $NH_3$ and then extracted thrice with diethyl ether. The combined ether portions were dried ($MgSO_4$), filtered, and the solvent removed in vacuo to give the crude residue that was used as is in the next reaction. GC-MS (70 eV) M=239 (81%).

b) (R)-3-(N-Cyclobutyl-N-isopropylamino)-8-fluoro-5-methoxy-3,4-dihydro-2H-1-benzopyran (R)-8-Fluoro-3-(N-isopropylamino)-5-methoxy-3,4-dihydro-2H-1-benzopyran (1.96 g, 8.19 mmol) was dissolved in anhydrous methanol (20 mL) and to this was cyclobutanone (6.1 mL, 81.9 mmol) added. The reaction was cooled (ice-bath) then sodium cyanoborohydride (2.0 g, 16.4 mmol) was added, the pH was adjusted to 4–5 with acetic acid, 3 Å molecular sieves were added and the reaction was allowed to stir at room temperature overnight. After 24 h the pH was again adjusted to 4–5 and the reaction was allowed to stir for 3 more days.

The reaction was filtered, solvent was removed in vacuo, the remains were taken into a 2M solution of $NH_3$ and then extracted thrice with diethyl ether. The combined ether portions were dried ($MgSO_4$), filtered, and the solvent removed in vacuo to give the crude residue.

Chromatography on silica (eluent: 10% ethyl acetate/hexane) gave 1.60 g (77% yield) of the title compound as a clear oil. $[\alpha]^{21}_D=-95.1°$ (C=0.1; CHCl3). GC-MS (70 eV) M=293 (3%).

c) (R)-3-(N-Cyclobutyl-N-isopropylamino)-8-fluoro-5-hydroxy-3,4-dihydro-2H-1-benzopyran (R)-3-(N-Cyclobutyl-N-isopropylamino)-8-fluoro-5-methoxy-3,4-dihydro-2H-1-benzopyran hydrochloride (1.76 g, 5.34 mmol) was dissolved in anhydrous $CH_2Cl_2$ (45 mL) and cooled to −40° C. To the solution was $BBr_3$ (1.3 mL, 13.4 mmol), dissolved in anhydrous $CH_2Cl_2$ (7 mL) added dropwise. The cooling-bath was removed and after 2 h at room temperature the reaction was complete.

The reaction was poured out onto an ice/2M $NH_3$ solution and the $CH_2Cl_2$ portion was separated, the aqueous layer re-extracted, twice, with $CH_2Cl_2$. The combined $CH_2Cl_2$ portions were dried ($MgSO_4$), filtered, and the solvent removed in vacuo to give the crude residue. Chromatography on silica (eluent: 30% ethyl acetate/hexane) gave 1.46 g (98% yield) of the title compound as a gum. $[\alpha]^{21}_D=-95.7°$ (C=0.1; CHCl3). GC-MS (70 eV) M=279 (0.7%).

The hydrochloride salt was made by dissolving the pure base in ether and adding dropwise an excess of an ethereal HCl solution. The salt was washed with diethyl ether to give a white solid Mp: 120° C. sinters.

d) (R)-3-(N-Cyclobutyl-N-isopropylamino)-8-fluoro-5-trifluoromethylsulfonyloxy-3,4-dihydro-2H-1-benzopyran (R)-3-(N-Cyclobutyl-N-isopropylamino)-8-fluoro-5-hydroxy-3,4-dihydro-2H-1-benzopyran (1.36 g, 4.87 mmol) and collidine (0.90 mL, 6.8 mmol) were dissolved in anhydrous $CH_2Cl_2$ (50 mL) and cooled to −40° C. Trifluoromethanesulfonic anhydride (1.05 mL, 6.1 mmol) was added dropwise and allowed to warm to ambient temperature, and after coming to 0° C. the reaction was done. The reaction was diluted with $CH_2Cl_2$ and washed with a saturated aqueous $NaHCO_3$ solution, the aqueous was re-extracted, twice, with $CH_2Cl_2$ the combined $CH_2Cl_2$ portions were dried ($MgSO_4$), filtered, and evaporated in vacuo to give a crude residue. Chromatography on silica (eluent: 70% hexane/$CH_2Cl_2$) gave 1.67 g (83% yield) of the title compound as a slightly yellow oil. $[\alpha]^{21}_D$=−86.8° (C=0.1; CHCl3). GC-MS (70 eV) M=411 (0.3%).

e) Methyl (R)-3-(N-Cyclobutyl-N-isopropylamino)-8-fluoro-3,4-dihydro-2H-1-benzopyran-5-carboxylate (R)-3-(N-Cyclobutyl-N-isopropylamino)-8-fluoro-5-trifluoromethylsulfonyloxy-3,4-dihydro-2H-1-benzopyran (1.65 g, 4.01 mmol) was dissolved in a solution of DMF/methanol (6:2, 30 mL) and then degassed followed by the inlet of carbon monoxide (×3). With a slight positive pressure of carbon monoxide, palladium(II)-acetate (30 mg), 1,3-bis(diphenylphosphino)propane (55 mg) and triethylamine (1.25 mL, 8.8 mmol) were added and the reaction mixture was degassed and subjected to carbon monoxide once again. The reaction was heated to 70° C. under carbon monoxide atmosphere with vigorous stirring for 6 h. The reaction was allowed to cool and the solvent was removed in vacuo. The remains were taken into a 2M solution of $NH_3$ and then extracted, twice, with diethyl ether. The combined ether portions were dried ($MgSO_4$), filtered, and the solvent removed in vacuo to give the crude residue. Chromatography on silica (eluent: 8% ethyl acetate/hexane) gave 1.18 mg (92% yield) of the title compound as a clear oil. $[\alpha]^{21}_D$=−139.1° (C=0.1; CHCl3). GC-MS (70 eV) M=321 (3%).

f) (R)-5-Carbamoyl-3-(N-cyclobutyl-N-isopropylamino)-8-fluoro-3,4-dihydro-2H-1-benzopyran Methyl (R)-3-(N-cyclobutyl-N-isopropylamino)-8-fluoro-3,4-dihydro-2H-1-benzopyran-5-carboxylate (1.16 g, 3.61 mmol) was refluxed with a 6M solution of HCl (30 mL) for 3.5 h. The solution was cooled, concentrated to dryness in vacuo and anhydrous toluene was added and the solvent was removed in vacuo (×4).

To the white gum was thionyl chloride (35 mL) added and the solution was allowed to stir at room temperature overnight. The excess thionyl chloride was removed in vacuo, anhydrous toluene added and the solvent removed in vacuo.

The acid chloride was dissolved in $CH_2Cl_2$ (50 mL) and added dropwise to a cooled solution (ice-bath) of concentrated $NH_3$ (50 mL). The reaction was allowed to stir at room temperature for 40 min. The $CH_2Cl_2$ phase was separated and the aqueous portion was re-extracted with $CH_2Cl_2$ (×3). The combined $CH_2Cl_2$ portions were dried ($MgSO_4$), filtered, and evaporated in vacuo to give the crude residue. Chromatography on silica (eluent: ethyl acetate) gave 1.06 g (95% yield) of a white foam. The foam was crystallized using $CH_2Cl_2$/hexane to give a white solid. Mp: 127.8–128.4° C. $[\alpha]^{21}_D$=−143.0° (C=0.1; CHCl3). GC-MS (70 eV) M=306 (0.3%).

The hydrochloride salt was made by dissolving the pure base in ether and adding dropwise an excess of an ethereal HCl solution. The salt was washed with diethyl ether to give a white solid. Mp: 120° C. sinters.

EXAMPLE 7

(R)-5-Carbamoyl-3-(N-cyclopentyl-N-n-propylamino)-8-fluoro-3,4-dihydro-2H-1-benzopyran a) (R)-3-(N-Cyclopentylamino)-8-fluoro-5-methoxy-3,4dihydro-2H-1-benzopyran To a solution of (R)-3-amino-8-fluoro-5-methoxy-3,4-dihydro-2H-1-benzopyran (2.5 g, 12 mmol), cyclopentanone (3.3 g, 36 mmol) and HOAc (0.7 g, 12 mmol) in methanol (25 mL) was $NaCNBH_3$ (2.5 g, 40 mmol) added in portions at room temperature. The solution was stirred at room temperature overnight to give a quantitative yield of the title compound. GC/MS (70 eV) M=265 (30%).

b) (R)-3-(N-Cyclopentyl-N-n-propylamino)-8-fluoro-5-methoxy-3,4-dihydro-2H-1-benzopyran To the solution of (R)-3-(N-cyclopentylamino)-8-fluoro-5-methoxy-3,4-dihydro-2H-1-benzopyran in methanol (25mL) were propanal (2 g, 36 mmol) and $NaCNBH_3$ (2 g, 40 mmol) added. The solution was stirred overnight to give the desired compound in a 97% yield according to GC. The solvent was removed in vacuo and the residue was worked up by extraction to give 3.7 g of the title compound as a colorless oil. GC/MS (70 eV) M=307 (40%).

c) (R)-3-(N-Cyclopentyl-N-n-propylamino)-8-fluoro-5-hydroxy-3,4-dihydro-2H-1-benzopyran The HCl salt of (R)-3-(N-cyclopentyl-N-n-propylamino)-8-fluoro-5-methoxy-3,4-dihydro-2-H-1-benzopyran was prepared by adding an excess of an ethereal HCl into an ethereal solution of the base. The solvent was evaporated in vacuo and the residue dissolved in 48% aqueous HBr (50 mL). The solution was stirred at 120° C. for 1.5 h. The solution was neutralized by carefully adding conc. ammonia. Extractive work-up gave a brown oil which was filtered through a plug of silica (ethyl acetate as the eluent). The title compound was isolated (3.7 g) as a slightly yellow oil. GC/MS (70 eV) M=293 (40%).

d) (R)-3-(N-Cyclopentyl-N-n-propylamino)-8-fluoro-5-trifluoromethylsulfonyloxy-3,4-dihydro-2H-1-benzopyran (R)-3-(N-Cyclopentyl-N-n-propylamino)-8-fluoro-5-hydroxy-3,4-dihydro-2H-1-benzopyran was dissolved in diethyl ether (100 mL). Triethylamine (3 g, 30 mmol) was added and the mixture was cooled to −20 ° C. Trifluoromethanesulfonic anhydride (4.2 g, 15 mmol), dissolved in diethyl ether (20 mL), was added dropwise (5 min). After stirring for 30 min, the dark-brownish mixture was poured into water. The organic layer was separated. Flash chromatography (ethyl acetate as the eluent) gave 3.7 g of the title compound as a yellow oil in a 69% yield. GC/MS (70 eV) M=425 (10%).

e) Methyl (R)-3-(N-Cyclopentyl-N-n-propylamino)-8-fluoro-3,4-dihydro-2H-1-benzopyran-5-carboxylate (R)-3-(N-Cyclopentyl-N-n-propylamino)-8-fluoro-5-trifluoromethylsulfonyloxy-3,4dihydro-2H-1-benzopyran (3.7 g, 8.7 mmol), DMF (50 mL), triethylamine (2.5 g, 25 mmol), methanol (4 g, 130 mmol), palladiuma(II)acetate (100 mg, 0.45 mmol) and 1,3bis(diphenylphosphino)propane (200 mg, 0.48 mmol) were placed in a round-bottomed flask. The solution was stirred at 75° C. in an atmosphere of carbon monoxide for 4 h. After evaporation of the solvent in vacuo and subjecting the crude to flash chromatography, 2.5 g (86 % yield) of the title compound as a colorless oil was isolated. GC/MS (70 eV) M=335 (20 %).

f) (R)-5-Carbamoyl-3-(N-cyclopentyl-N-n-propylamino)-8-fluoro-3,4-dihydro-2H-1-benzopyran Methyl (R)-3-(N-cyclopentyl-N-n-propylamino)-8-fluoro3,4-dihydro-2H-1-benzopyran-5-carboxylate (1.4 g, 4 mmol) was hydrolysed (6M HCl, refluxed for 2 h) and the solvent was removed in vacuo. The crude acid was treated with $SOCl_2$ (room temperature for 5 min) to form the acid chloride which after removal of excess $SOCl_2$ in vacuo was added to conc. ammonia to form the amide. The crude product was isolated and purified by flash chromatography. The HCl salt was prepared by adding an excess of ethereal HCl into an ethereal solution of the pure base to afford the title compound (0.5 g, yield 35%) as white crystals. Mp: 85° C. dec. $[\alpha]^{20}_D$ (base)=−91° (C=0.2; $CH_2Cl_2$). GC/MS (70 eV) M=320 (25%).

EXAMPLE 8

(R)-5-Carbamoyl-3-(N-cyclohexyl-N-n-propylamino)-8-fluoro-3,4-dihydro-2H-1-benzopyran a) (R)-3-(N-Cyclohexylamino)-8-fluoro-5-methoxy-3,4-dihydro-2H-1-benzopyran To a solution of (R)-3-amino-8fluoro-5-methoxy-3,4-dihydro-2H-1-benzopyran (0.45 g, 2.2 mmol), cyclohexanone (0.7 g, 7.2 mmol) and HOAc (0.14 g, 2.3 mmol) in methanol (25 mL) was NaCNBH$_3$ (0.5 g, 8 mmol) added in portions at room temperature. The solution was stirred at room temperature overnight to give a quantitative yield of the title compound. GC/MS (70 eV) M=279 (30%).

b) (R)-3-(N-Cyclohexyl-N-n-propylamino)-8-fluoro-5-methoxy-3,4-dihydro-2H-1-benzopyran To the solution of (R)-3-(N-cyclohexylamino)-8-fluoro-5-methoxy-3,4-dihydro-2H-1-benzopyran in methanol (25 mL) were propanal (1.3 g, 23 mmol) and NaCNBH$_3$ (0.15 g, 2.3 mmol) added. The solution was stirred overnight to give the desired compound in a 97% yield according to GC. The solvent was removed in vacuo and the residue was worked up by extraction to give 0.7 g of the title compound as a colorless oil. GC/MS (70 eV) M=321 (40%).

c) (R)-3-(N-Cyclohexyl-N-n-propylamino)-8-fluoro-5-hydroxy-3,4-dihydro-2H-1-benzopyran The HCl salt of the (R)-3-(N-cyclohexyl-N-n-propylamino)-8-fluoro-5-methoxy-3,4-dihydro-2-H-1-benzopyran was prepared by adding an excess of an ethereal HCl into ethereal solution of the base. The solvent was evaporated in vacuo and the residue dissolved in 48% aqueous HBr (20 mL). The solution was stirred at 120° C. for 1.5 h. The solution was neutralized by carefully adding conc. ammonia. Extractive work-up gave a brown oil which was filtered through a plug of silica (ethyl acetate as the eluent). The title compound was isolated (0.6 g) as a slightly yellow oil. GC/MS (70 eV) M=307 (40%).

d) (R)-3-(N-Cyclohexyl-N-n-propylamino)-8-fluoro-5-trifluoromethylsulfonyloxy-3,4-dihydro-2H-1-benzopyran (R)-3-(N-Cyclohexyl-N-n-propylamino)-8-fluoro-5-hydroxy-3,4-dihydro-2H-1-benzopyran was dissolved in diethyl ether (30 mL) and triethylamine (0.8 g, 8 mmol) was added and the mixture was cooled to –20 ° C. Trifluoromethanesulfonic anhydride (0.8 g, 2.8 mmol), dissolved in diethyl ether (10 mL), was added dropwise (5 min). After stirring for 30 min, the dark-brownish mixture was poured into water. The organic layer was separated. Flash chromatography (EtOAc/hexane 1+1 as the eluent) gave 0.8 g of the title compound as a yellow oil. GC/MS (70 eV) M=439 (20%).

e) Methyl (R)-3-(N-Cyclohexyl-N-n-propylamino)-8-fluoro-3,4-dihydro-2H-1-benzopyran-5-carboxylate (R)-3-(N-Cyclohexyl-N-n-propylamino)-8-fluoro-5-trifluoromethylsulfonyloxy-3,4dihydro-2H-1-benzopyran (0.8 g, 1.8 mmol) (4), DMF (30 mL), triethylamine (0.5 g, 5 mmol), methanol (0.8 g, 13 mmol), palladium(II)acetate (30 mg, 0.14 mmol) and 1,3-bis(diphenylphosphino) propane (60 mg, 0.14 mmol) were placed in a round-bottomed flask. The solution was stirred at 75 ° C. in an atmosphere of carbon monoxide for 4 h. After evaporation of the solvent in vacuo and subjecting the crude to flash chromatography, 0.6 g (76% yield) of the title compound as a colorless oil was isolated. GC/MS (70 eV) M=349 (30 %).

f) (R)-5-Carbamoyl-3-(N-cyclohexyl-N-n-propylamino)-8-fluoro-3,4-dihydro-2H-1-benzopyran Methyl (R)-3-(N-cyclohexyl-N-n-propylamino)-8-fluoro-3,4-dihydro-2H-1-benzopyran-5-carboxylate (5) (0.6 g, 1.7 mmol) was subjected to alkaline hydrolysis (2% KOH in EtOH, refluxed for 2 h). The solvent was removed in vacuo and the crude add was treated with SOCl$_2$ (room temperature for 5 min) to form the acid chloride which after removal of excess SOCl$_2$ in vacuo was added to conc. ammonia to form the amide. The crude product was isolated and purified by flash chromatography. The HCl salt was prepared by adding an excess of ethereal HCl into an ethereal solution of the pure base to afford the title compound (86 mg, yield 14%) as white crystals. Mp: 75° C. dec. $[\alpha]^{20}_D$=–73° (C=0.2, CH$_2$Cl$_2$). GC/MS (70 eV) M=334 (35%).

EXAMPLE 9

(R)-5-Carbamoyl-3-(N-cyclopentyl-N-cyclobutylamino)-8-fluoro-3,4-dihydro-2H-1-benzopyran a) (R)-3-(N-Cyclopentylamino)-8-fluoro-5-methoxy-3,4-dihydro-2H-1-benzopyran To a solution of (R)-3-amino-8-fluoro-5-methoxy-3,4dydro-2H-1-benzopyran (0.7 g, 3.4 mmol), cyclopentanone (0.7 g, 8.3 mmol) and HOAc (0.2 g, 3.5 mmol) in methanol (25 mL), NaCNBH$_3$ (0.7 g, 10 mmol) was added in portions at room temperature. The solution was stirred at room temperature over night. The methanol was evaporated. The residue was dissolved in EtOAc and washed with water. The organic layer was dried with Na$_2$SO$_4$ and the solvent was evaporated to give 0.9 g (100% yield) of the title compound as a colourless oil. GC indicated 99.6 purity. GC/MS (70 eV) M=265 (30%).

b) (R)-3-(N-Cyclopentyl-N-cyclobutylamino)-8-fluoro-5-methoxy-3,4-dihydro-2H-1-benzopyran To a solution of (R)-3-(N-cyclopentylamino)-8-fluoro-5-methoxy-3,4-dihydro-2H-1-benzopyran (0.9 g, 3.4 mmol), HOAc (0.22 g, 3.6 mmol) and cyclobutanone (2g, 30 mmol) in methanol (25 mL), were NaCNBH$_3$ (1 g, 16 mmol) added in portions at room temperature. After stirring for four days GC indicated 37% product. pH was adjusted to 5 (HOAc) and additional (1 g, 15 mmol) cyclobutanone was added. After stirring for further 6 days, GC indicated 64% conversion. The solvent was evaporated and the residue worked up by extraction. Flash chromatography (EtOAc/P-ether, 1+1), gave 0.53 g (53% yield) of the title compound as a colourless oil. GC/MS (70 eV) M=319 (3%).

c) (R)-3-(N-Cyclopentyl-N-cyclobutylamino)-8-fluoro-5-hydroxy-3,4-dihydro-2H-1-benzopyran (R)-3-(N-Cyclopentyl-N-cyclobutylamino)-8-fluoro-5-methoxy-3,4dihydro-2H-1-benzopyran (0.53 g, 1.6 mmol) was dissolved in 47% HBr (15 mL) and stirred at 120° C. for 1.5 h. The solution was cooled by adding ice and alkalised by 14M ammonia. Extractive work-up gave 0.5 g of the title compound as a slightly brown oil. IR contained a typical OH-band at 3654 cm$^{-1}$.

d) (R)-3-(N-Cyclopentyl-N-cyclobutylamino)-8-fluoro-5-trifluoromethylsulfonyloxy-3,4-dihydro-2H-1-benzopyran (R)-3-(N-Cyclopentyl-N-cyclobutylamino)-8-fluoro-5-hydroxy-3,4-dihydro-2H-1-benzopyran was dissolved in a mixture of diethyl ether and methylene chloride (90+10, 20 mL) and triethylamine (0.7 g, 7 mmol) was added and the mixture was cooled to –20 ° C. Trifluoromethanesulfonic anhydride (0.85 g, 3 mmol), dissolved in diethyl ether (10 mL), was added dropwise (5 min). After stirring for 30 min, the dark-brownish mixture was poured into water. The solvent was evaporated. The residue was dissolved in hexane and treated with active charcoal. Filtration trough celite and evaporation of the solvent afforded 0.67 g of the title compound as a colorless oil. GC/MS (70 eV) M=437 (1%).

e) Methyl (R)-3-(N-Cyclopentyl-N-cyclobutylamino)-8-fluoro-3,4-dihydro-2H-1-benzopyran-5-carboxylate (R)-3-(N-Cyclopentyl-N-cyclobutylamino)-8-fluoro-5-trifluoromethylsulfonyloxy-3,4-dihydro-2H-1-benzopyran (0.67 g, 1.5 mmol) (4), DMF (20 mL), triethylamine (0.6 g, 6 mmol), methanol (0.8 g, 12.7 mmol), palladium(II)acetate (22 mg, 0.1 mmol) and 1,3-bis(diphenylphosphino)propane (44 mg, 0.1 mmol) were placed in a round-bottomed flask. The solution was stirred at 75° C. in an atmosphere of carbon monoxide for 4 h. The solvent was removed in vacuo, the residue was dissolved in diethyl ether and treated with active charcoal. Evaporation of the solvent afforded 380 mg of the title compound as an uncolored oil. GC/MS (70 eV) M=347 (3 %).

f) (R)-5-Carbamoyl-3-(N-cyclopentyl-N-cyclobutylamino)-8-fluoro-3,4-dihydro-2H-1-benzopyran Methyl (R)-3(N-cyclopentyl-N-cyclobutylamino)-8-fluoro-3,4-dihydro-2H-1-benzopyran-5-carboxylate (1.4 g, 4 mmol) was hydrolysed (6M HCl, refluxed for 2 h) and the solvent was removed in vacuo. After drying in air at room temperature over night the crude amino acid hydrochloride was treated with $SOCl_2$ (room temperature for 5 min) to form the acid chloride which after removal of excess $SOCl_2$ in vacuo was dissolved in $CH_2Cl_2$ and added to conc. ammonia to form the amide. The crude product was isolated and purified by flash chromatography to give 220 mg of an uncolored oil which crystallized upon standing. Recrystallization from a mixture of diethyl eter and hexane gave white crystals of the title compound. Yield: 110 mg. Mp: 138–140° C. $[\alpha]^{20}_D = -146°$ (C=0.2, $CH_2Cl_2$).

Pharmacology
Methods for testing (i) 5-$HT_{1A}$ receptor binding assay

In order to evaluate the affinity for the 5-$HT_{1A}$-receptor the assay described below using rat brain can be used.

Tissue preparation: Cerebral cortex and hippocampus from Sprague-Dawley rats are dissected and homogenized in 15 ml ice-old 50 mM Tris-HCl buffer, pH 7.5, containing 4.0 mM $CaCl_2$ and 5.7 mM ascorbic acid ("Buffer A") with an Ultra-Turrax (Janke & Kunkel, Staufen, FRG) for ten sec. After centrifugation for 12.5 min at 17,000 rpm (39,800×g in a Beckman centrifuge with a chilled JA-17 rotor (Beckman, Palo Alto, Calif., USA)), the pellets are resuspended in buffer A and homogenization and centrifugation repeated. Each pellet is suspended in 5 ml ice-cold 0.32M sucrose and homogenized for 5 sec. The homogenized samples are kept frozen at −70° C. When used, they are diluted with buffer A to 8 mg tissue/ml and homogenized for 10 sec. The tissue homogenates are incubated for ten min at 37° C. and then supplied with 10 μm pargyline followed by reincubation for 10 min.

The binding assay followed that described by Peroutka, *J. Neurochem.* 47, 529–540, (1986). Essentially this assay measures the ability of a given competitor molecule to inhibit the binding of $^3H$-8-OH-DPAT to 5-$HT_{1A}$ receptors. The incubation mixture (2 ml) contained $^3H$-8-OH-DPAT (0.25 to 8 nM), the desired concentration of test (competitor) compound and 5 mg/ml tissue homogenate in 50 mM Tris-CH1 buffer, pH 7.5, containing 4.0 mM $CaCl_2$ and 5.7 mM ascorbic add. Six different concentrations of $^3H$-8-OH-DPAT are analyzed. Binding experiments are started by the addition of tissue homogenate and followed by incubation at 37° C. for ten min. The incubation mixtures are filtered through Whatman GF/B glass filters with a Brandel Cell Harvester (Gaithersburg, Md., USA). The filters are washed twice with 5 ml ice-cold 50 mM Tris-HCl buffer, pH 7.5, and counted with 5 ml Ultima Gold™ (Packard) in a Beckman LS 3801 scintillation counter. Nonspecific binding is measured by the addition of 10 μM 5-HT to the reaction mixture. The binding data is processed by non-linear least squares computer analysis (Munson and Rodbard, Anal. Biochem. 107, 220–239, (1980)).

(ii) Antagonism of 8-OH-DPAT induced decrease in 5-HT synthesis via blockade of presynaptic 5-$HT_{1A}$ receptors.

The rate of synthesis of 5-hydroxytryptamine (5-HT: serotonin) and dopamine/noradrenaline (DA/NA) is measured as the accumulation of 5-hydroxytryptophan (5-HTP) and 3,4-dihydroxyphenylalanine, (DOPA) respectively during 30 min after inhibition of aromatic L-amino acid decarboxylase by m-hydroxbenzylhydrazine 2HCl (100 mg/kg i.p.); purchased from Sigma. The test substance is administrated 75 min before, 8-OH-DPAT 60 min before and m-hydroxybenzylhydrazine*2HCl 30 min before the rats were killed. The regions of the brain to be examined are rapidly dissected, frozen on dry ice and stored at −70° C until assayed.

DOPA, 5-HTP and their metabolites are extracted from brain tissue with perchloric acid, containing an internal standard (Isoprenalin), The supernatant from brain homogenate is injected into a liquid chromatographic system comprising a precolumn and an analytical column. The catechol- and indolamines are detected by coulometric oxidation.

(iii) Antagonism of the acute 5HT reuptake inhibitor (SSRI) induced decrease in 5-HT turnover by selective 5-$HT_{1A}$ antagonists.

Animals

Male Sprague-Dawley rats (B&K International AB, Sollentuna, Sweden), weighing 180–220 g, are housed 5 per cage under controlled temperature (21° C.) and humidity with a 12 hr light-dark cycle (lights on 6 a.m.). Food and water are freely available. They are kept under these conditions at . least four days prior to the experimentation. The compounds are administered orally (po) or subcutaneously (sc).

5-HT turnover

Groups of 5 rats are administered with the 5-$HT_{1A}$ antagonist 15 min before the injection of the 5-HT reuptake inhibitor (e.g. norzimeldine=(Z)-3-(4-Bromophenyl)-N-methyl-3-(3-pyridyl)-allylamine, dihydrochloride monohydrate). m-Hydroxybenzylhydrazine*2HCl(NSD 1015) is injected 30 min. later and the rats are killed with a guillotine 30 min after injection of the reuptake inhibitor (NSD 1015). Brains are rapidly removed and the regions dissected are immediately frozen on dry ice. The samples are stored at −70° until assayed.

The endogenous compounds, 5-HT and 5-HT1A in various brain regions are determined by use of high performance liquid chromatography (HPLC) with electrochemical detection according to the method of Magnusson (*J. Chromatogr.* 1980; 221:237–247). The mobile phase is 0.1M phosphate buffer (pH 2.5): methanol: acetonitrile −89:9:2 v/v, containing 1 nM octylsulphate. The frozen samples are weighed and homogenized in 0.1M perchloric acid, containing 2.5 nM sodium bisulphite, 1 nM ethylendiaminetetraacetic add (EDTA). The supernatants are injected directly onto a Supelcosil $C_{18}$ (3 μM) column, connected to a detector (ESA Coulochem 5100A), set to 0.05/0.30 V. The catechol- and indoleamines are detected by coulornetric oxddation.

Figure 1:
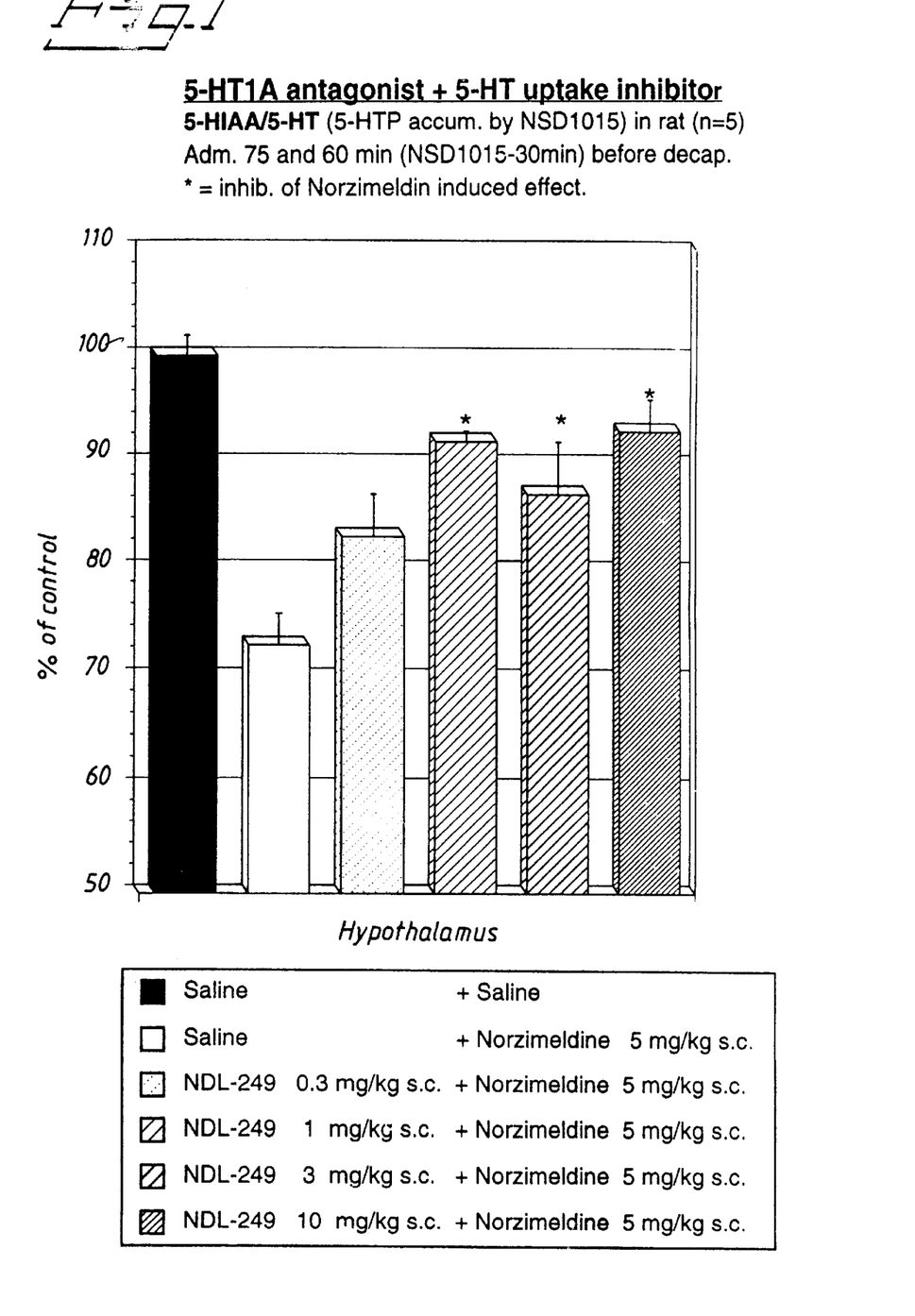
FIG. 1 shows the effect in rats of combining a $5\text{-HT}_{1A}$ antagonist with a 5-HT reuptake inhibitor.

FIG. 1 shows that blocking 5-HT1A somatodendritic receptors by a selective antagonist such as (R)-3-(N-Cyclopentyl-N-n-propylamino)-8-fluoro-5-N- methylcarbamoyl-3,4-dihydro-2H-1-benzopyran (Example 1; NDL 249), augments in a dose-dependent way the antidepressant efficacy of 5-HT uptake blockers by enabling serotonenergic terminals to release more 5-HT and thereby causing a basis for a rapid onset of therapeutic actions.

We claim:

1. A combination of a first component (a) which is a 5-HT reuptake inhibitor and a second component (b) which is a selective 5-HT$_{1A}$ antagonist of the formula (I)

wherein
   R$_1$ is n-propyl or cyclobutyl;
   R$_2$ is isopropyl, tertiary butyl, cyclobutyl, cyclopentyl or cyclohexyl;
   R$_3$ is hydrogen;
   R$_4$ is hydrogen or methyl;
said 5-HT$_{1A}$-antagonist being in the form of its R-enantiomer, and said components (a) and (b) being in the form of their free bases or pharmaceutically acceptable salts thereof.

2. The combination according to claim 1 wherein the selective 5-HT$_{1A}$ antagonist is (R)-3-(N-tert-butyl-N-n-propylamino)-5-carbamoyl-8-fluoro-3,4-dihydro-2H-1-benzopyran in the form of its free base or a pharmaceutically acceptable salt thereof.

3. The combination according to claim 1 wherein the 5-HT$_{1A}$ antagonist is (R)-5-carbamoyl-3-(N,N-dicyclobutylamino)-8-fluoro-3,4-dihydro-2H-1-benzopyran in the form of its free base or a pharmaceutically acceptable salt thereof.

4. The combination according to claim 1 wherein the 5-HT$_{1A}$ antagonist is (R)-5-carbamoyl-3-(N-cyclobutyl-N-n-propylamino)-8-fluoro-3,4-dihydro-2H-1-benzopyran in the form of its free base or a pharmaceutically acceptable salt thereof.

5. The combination according to claim 1 wherein the 5-HT$_{1A}$ antagonist is (R)-5-carbamoyl-3-(N-cyclobutyl-N-isopropylamino)-8-fluoro-3,4-dihydro-2H-1-benzopyran in the form of its free base or a pharmaceutically acceptable salt thereof.

6. The combination according to claim 1 wherein the 5-HT$_{1A}$ antagonist is (R)-5-carbamoyl-3-(N-cyclopentyl-N-n-propylamino)-8-fluoro-3,4-dihydro-2H-1-benzopyran in the form of its free base or a pharmaceutically acceptable salt thereof.

7. The combination according to claim 1 wherein the 5-HT$_{1A}$ antagonist is (R)-5-carbamoyl-3-(N-cyclopentyl-N-cyclobutylamino)-8-fluoro-3,4-dihydro-2H-1-benzopyran in the form of its free base or a pharmaceutically acceptable salt thereof.

8. The combination according any one of claims 1–7 wherein the 5-HT reuptake inhibitor is fluoxetine.

9. A process for the preparation of a combination of a 5-HT reuptake inhibitor and a selective 5-HT$_{1A}$ antagonist, which comprises incorporating a 5-HT reuptake inhibitor into the same pharmaceutical formulation as a selective 5-HT$_{1A}$ antagonist as defined in any one of claims 1–7.

10. A process for the preparation of a combination of a 5-HT reuptake inhibitor and a selective 5-HT$_{1A}$ antagonist whereby a 5-HT reuptake inhibitor in a first pharmaceutical formulation is combined with a selective 5-HT$_{1A}$ antagonist as defined in any one of claims 1–7 in a second pharmaceutical formulation.

11. A kit containing the combination of a first component (a) which is a 5-HT reuptake inhibitor and a second component (b) which is a selective 5-HT$_{1A}$ antagonist according to claim 1 optionally with instructions for use.

12. A method of improving the onset of therapeutic action which comprises coadministration of a first component (a) which is a 5-HT reuptake inhibitor and a second component (b) which is a selective 5-HT$_{1A}$ antagonist as described in claim 1.

13. The combination according to any one of claims 1–7 wherein the 5-HT reuptake inhibitor is paroxetine.

14. The combination according to any one of claims 1–7 wherein the 5-HT reuptake inhibitor is citalopram.

15. The combination according to any one of claims 1–7 wherein the 5-HT reuptake inhibitor is clomipramine.

16. The combination according to any one of claims 1–7 wherein the 5-HT reuptake inhibitor is sertraline.

17. The combination according to any one of claims 1–7 wherein the 5-HT reuptake inhibitor is fluvoxamine.

18. The combination of the selective 5-HT$_{1A}$ antagonist (R)-5-carbamoyl-3-(N,N-dicyclobutylamino)-8-fluoro-3,4-dihydro-2H-1-benzopyran in the form of its free base or a pharmaceutically acceptable salt thereof and the 5-HT reuptake inhibitor fluoxetine.

19. The combination of the selective 5-HT$_{1A}$ antagonist (R)-5-carbamoyl-3-(N,N-dicyclobutylamino)-8-fluoro-3,4-dihydro-2H-1-benzopyran in the form of its free base or a pharmaceutically acceptable salt thereof and the 5-HT reuptake inhibitor paroxetine.

20. The combination of the selective 5-HT$_{1A}$ antagonist (R)-5-carbamoyl-3-(N,N-dicyclobutylamino)-8-fluoro-3,4-dihydro-2H-1-benzopyran in the form of its free base or a pharmaceutically acceptable salt thereof and the 5-HT reuptake inhibitor citalopram.

21. The combination of the selective 5-HT$_{1A}$ antagonist (R)-5-carbamoyl-3-(N,N-dicyclobutylamino)-8-fluoro-3,4-dihydro-2H-1-benzopyran in the form of its free base or a pharmaceutically acceptable salt thereof and the 5-HT reuptake inhibitor clomipramine.

22. The combination of the selective 5-HT$_{1A}$ antagonist (R)-5-carbamoyl-3-(N,N-dicyclobutylamino)-8-fluoro-3,4-dihydro-2H-1-benzopyran in the form of its free base or a pharmaceutically acceptable salt thereof and the 5-HT reuptake inhibitor sertraline.

23. The combination of the selective 5-HT$_{1A}$ antagonist (R)-5-carbamoyl-3-(N,N-dicyclobutylamino)-8-fluoro-3,4-dihydro-2H-1-benzopyran in the form of its free base or a pharmaceutically acceptable salt thereof and the 5-HT reuptake inhibitor fluvoxamine.

24. A method for the treatment of affective disorders which comprises administering to a patient suffering therefrom an effective amount of the combination defined in any one of claims 1–7 and 18–23.

25. A method for the treatment of depression which comprises administering to a patient suffering therefrom an effective amount of the combination defined in any one of claims 1–7 and 18–23.

26. A pharmaceutical formulation for use in the treatment of affective disorders wherein the active ingredients are the combination defined in any one of claims 1–7 and 18–23 optionally with diluents, excipients and/or inert carriers.

27. A pharmaceutical formulation according to claim 26 for use in the treatment of depression.

* * * * *